United States Patent
Qiao et al.

(10) Patent No.: US 9,633,307 B2
(45) Date of Patent: Apr. 25, 2017

(54) METHOD TO PREDICT THE EFFLUENT AMMONIA-NITROGEN CONCENTRATION BASED ON A RECURRENT SELF-ORGANIZING NEURAL NETWORK

(71) Applicant: BEIJING UNIVERSITY OF TECHNOLOGY, Beijing (CN)

(72) Inventors: Junfei Qiao, Beijing (CN); Ying Hou, Beijing (CN); Honggui Han, Beijing (CN); Wenjing Li, Beijing (CN)

(73) Assignee: BEIJING UNIVERSITY OF TECHNOLOGY, Beijing (CN)

( * ) Notice: Subject to any disclaimer, the term of this patent is extended or adjusted under 35 U.S.C. 154(b) by 75 days.

(21) Appl. No.: 14/668,836

(22) Filed: Mar. 25, 2015

(65) Prior Publication Data

US 2016/0140437 A1 May 19, 2016

(30) Foreign Application Priority Data

Nov. 17, 2014 (CN) .......................... 2014 1 0655729

(51) Int. Cl.
*G06N 3/08* (2006.01)
*G01N 33/18* (2006.01)
(Continued)

(52) U.S. Cl.
CPC ............. *G06N 3/088* (2013.01); *C02F 3/006* (2013.01); *G01N 33/18* (2013.01); *G06N 3/0445* (2013.01); *C02F 2101/16* (2013.01); *C02F 2209/001* (2013.01); *C02F 2209/006* (2013.01); *C02F 2209/04* (2013.01); *C02F 2209/10* (2013.01); *C02F 2209/14* (2013.01);
(Continued)

(58) Field of Classification Search
None
See application file for complete search history.

(56) References Cited

U.S. PATENT DOCUMENTS

| 8,216,517 B2 * | 7/2012 | Prasad | G05B 13/048 210/614 |
| 8,252,182 B1 * | 8/2012 | Chang | B01J 20/10 210/170.08 |
| 2015/0053612 A1 * | 2/2015 | Bitan-Banin | C02F 3/006 210/613 |

OTHER PUBLICATIONS

Chen et al., Assessing wastewater reclamation potential by neural network model, 2003, Engineering Applications of Artificial Intelligence, 16, pp. 149-157.*

* cited by examiner

*Primary Examiner* — Alan Chen
(74) *Attorney, Agent, or Firm* — J.C. Patents

(57) ABSTRACT

An intelligent method is designed for predicting the effluent ammonia-nitrogen concentration in the urban wastewater treatment process (WWTP). The technology of this invention is part of advanced manufacturing technology, belongs to both the field of control engineering and environment engineering. In order to improve the predicting efficiency, a recurrent self-organizing neural network, which can adjust the structure and parameters concurrently to train the parameters, is developed to design this intelligent method. This intelligent method can predict the effluent ammonia-nitrogen concentration with acceptable accuracy and solve the problem that the effluent ammonia-nitrogen concentration is difficult to be measured online. Moreover, the online information of effluent ammonia-nitrogen concentration, predicted by this intelligent method, can enhance the quality monitoring level and alleviate the current situation of wastewater to strengthen the whole management of WWTP.

12 Claims, 3 Drawing Sheets

(51) Int. Cl.
*G06N 3/04* (2006.01)
*C02F 3/00* (2006.01)
*C02F 101/16* (2006.01)

(52) U.S. Cl.
CPC ...... *C02F 2209/18* (2013.01); *C02F 2209/22* (2013.01); *C02F 2209/40* (2013.01)

METHOD TO PREDICT THE EFFLUENT AMMONIA-NITROGEN CONCENTRATION BASED ON A RECURRENT SELF-ORGANIZING NEURAL NETWORK

CROSS-REFERENCE TO RELATED APPLICATION

This application claims the priority benefit of China patent application serial No. 201410655729.2, filed on Nov. 17, 2014, the content of which is herein incorporated by reference and made a part of the specification.

TECHNICAL FIELD OF THE INVENTION

This invention is directed to a method, based on the recurrent self-organizing neural network, to predict the effluent ammonia-nitrogen concentration in the urban wastewater treatment process (WWTP). The effluent ammonia-nitrogen concentration is critical to wastewater nitrogen removal, and therefore it is one of the most important parameters to evaluate the degree of urban WWTP. In general, the technology of this invention is part of advanced manufacturing technology, belongs to both the field of control engineering and environment engineering.

TECHNICAL BACKGROUND

Recently, the increased awareness about the negative impact of eutrophication in the quality of water bodies and the advances in environmental technology have given rise to more stringent wastewater treatment requirements and regulations. Nitrification is implemented in many urban WWTP to maintain an effluent ammonia-nitrogen concentration lower than a permit level, and often as a precursor to denitrification where there is an effluent ammonia-nitrogen concentration limit. Effluent limits are typically applied because residual ammonia may cause a critical oxygen deficit in the receiving water, potentially resulting in harm to the environment. Additionally, at high pH levels and high temperatures, the ammonium/ammonia equilibrium favors a greater free ammonia concentration, which may be toxic for aquatic and marine biota.

The subsequent increase in operational and management investments stimulates modern urban WWTPs to face the challenges of maintaining and improving effluent quality, while guaranteeing efficient and safe operations. A major requirement for achieving these goals relies on the availability of online measurements of effluent ammonia-nitrogen concentration. The online measurements of effluent ammonia-nitrogen concentration are efficient for monitoring the operation of the plants with immediate implications for environmental compliance, safety, management planning and profitability.

Moreover, the online measurement of effluent ammonia-nitrogen concentration is invaluable for an effective utilization of advanced process control and optimization strategies in urban WWTP. However, traditionally, the measurement of effluent ammonia-nitrogen concentration is performed according to a standardized method, where the protocol consists of putting the samples potentially contaminated with organic matter into specific bottles, aerating them, and adding a microbial population. This off-line laboratory measurement requires several hours. And the harsh conditions in biological treatment processes such as the activated sludge process make reliable field measurements challenging. Therefore, although the effluent ammonia-nitrogen concentration can be measured by laboratory analyses, a significant time delay in the range of minutes to hours is usually unavoidable. These results are normally too late to achieve well-timed adaptive process control accommodating influent fluctuation and other disturbances, especially for advanced wastewater treatment requiring more precise and timely controls. During the recent decades, considerable development in online instrumentation has taken place. In spite of the recent advances, such as in situ nutrient sensors and dissolved oxygen sensors, instruments still tend to get fouled. Nevertheless, trustworthy online measurement of effluent ammonia-nitrogen concentration is not there yet.

According to the above analysis, the existing detection methods of effluent ammonia-nitrogen concentration are difficult to meet the requirements of urban WWTP. Moreover, lack of suitable online sensors for monitoring the effluent ammonia-nitrogen concentration limits the effective control of effluent quality especially in urban WWTP. Therefore, a new online and accuracy detection method for the effluent ammonia-nitrogen concentration is like to be studied.

To obtain more reliable information on the effluent ammonia-nitrogen concentration in urban WWTP, we have investigated an intelligent method based on the recurrent self-organizing neural network. The objective of this patent is to develop an intelligent method for estimating the effluent ammonia-nitrogen concentration online and with high accuracy.

SUMMARY

In this invention an intelligent method based on a recurrent self-organizing neural network is proposed for online estimation of effluent ammonia-nitrogen concentration in urban WWTP. In order to improve the estimation performance, a growing and pruning method, based on the sensitivity analysis of hidden nodes, is developed to construct the recurrent neural network. The redundant hidden nodes will be removed and the new hidden nodes will be inserted when the contribution ratios of hidden nodes meet the criteria. Then, the structure of the recurrent neural network is able to be self-organized to maintain the estimation accuracy. This patent realizes the online measurement of effluent ammonia-nitrogen concentration, improves the efficiency to monitor the operation of the plants.

According to an embodiment of the invention, the following technical scheme and implementation steps are adopted:

An intelligent method for the effluent ammonia-nitrogen concentration based on a recurrent self-organizing neural network is provided according to an embodiment of the present invention, its characteristic and steps include the following steps:

(1) Select input variables

Learning from the work experience in operating urban WWTP and our analysis of its detailed mechanism, a total of five process variables have been chosen as the input variables to develop the intelligent method: total phosphorus (TP), oxidation reduction potential (ORP), dissolved oxygen (DO), total suspended solids (TSS), and the effluent pH, respectively.

(2) Design the recurrent self-organizing neural network

The recurrent self-organizing neural network consists of three layers: input layer, hidden layer and output layer. The initial structure is 5-K-1. There are 5 nodes in the input layer, K nodes in the hidden layer and 1 node in the output layer, K>2 is a positive integer. The number of training samples is T. The input vector of the recurrent self-organizing neural network is $u(t)=[u_1(t), u_2(t), u_3(t), u_4(t), u_5(t)]$ at time t. $u_1(t)$ is the value of TP, $u_2(t)$ is the value of ORP, $u_3(t)$ is the value of DO, $u_4(t)$ is the value of TSS, and $u_5(t)$ is the value of effluent pH at time t respectively. $y(t)$ is the output of the recurrent self-organizing neural network, and $y_d(t)$ is the real value of the effluent ammonia-nitrogen concentration at time t respectively. The output of the recurrent self-organizing neural network can be described:

$$y(t) = \sum_{k=1}^{K} w_k^3(t) v_k(t), \tag{1}$$

where $w_k^3(t)$ is the connecting weight between the kth hidden node and the output node at time t, $k=1, 2, \ldots, K$; and $v_k(t)$ is the output of the kth hidden layer at time t:

$$v_k(t) = f\left(\sum_{m=1}^{5} w_{mk}^1(t) u_m(t) + v_k^1(t)\right), \tag{2}$$

$w_{mk}^1(t)$ is the connecting weight between the mth node in the input layer and the kth hidden node at time t, $m=1, 2, \ldots, 5$; $v_k^1(t)$ is the feedback value of the kth hidden node at time t which can be described as:

$$v_k^1(t) = w_k^2(t) v_k(t-1), \tag{3}$$

$w_k^2(t)$ is the self-feedback weight of the kth hidden node at time t, $v_k(t-1)$ is the output of the kth hidden layer at time $t-1$;

Moreover, the root-mean-squared error is defined:

$$E(t) = \frac{1}{2T} \sum_{t=1}^{T} (y_d(t) - y(t))^2, \tag{4}$$

where T is the number of the training samples.

(3) Train the recurrent self-organizing neural network

① Initialize the connecting weights between the hidden nodes and the output node, the self-feedback weights of the hidden nodes, and the connecting weights between the nodes in the input layer and the hidden nodes, $w_k^3(t)\in(0, 1)$, $w_k^2(t)\in(0, 1)$, and $w_{mk}^1(t)\in(0, 1)$, $m=1, 2, \ldots, 5$, $k=1, 2, \ldots, K$, pre-set the expected error value $E_d$, $E_d\in(0, 0.01]$.

② Calculate the total sensitivity of hidden nodes:

$$ST_k(t) = \frac{\mathrm{Var}_k[E(y(t)|v_k(t))]}{\mathrm{Var}[y(t)]}, \text{ where} \tag{5}$$

$$\mathrm{Var}_k[E(y(t)|v_k(t))] = 2(A_k)^2 + (B_k)^2, \tag{6}$$

$$\mathrm{Var}(y(t)) = 2\sum_{k=1}^{K}((A_k)^2 + (B_k)^2),$$

$k=1, 2, \ldots, K$; $A_k$ and $B_k$ are the Fourier coefficients which are given by:

$$A_k = \frac{1}{2\pi}\int_{-\pi}^{\pi} \cos(\omega_k(t)s) ds, \tag{7}$$

$$B_k = \frac{1}{2\pi}\int_{-\pi}^{\pi} \sin(\omega_k(t)s) ds,$$

where the range of s is $[-\pi, \pi]$; $\omega_k(t)$ is the frequency of the kth hidden node, $\omega_k(t)$ is decided by the output of the kth hidden node:

$$\omega_k(t) = \arcsin\frac{\pi}{b_k(t)-a_k(t)}\left(v_k(t) - \frac{b_k(t)+a_k(t)}{2}\right), \tag{8}$$

where $b_k(t)$ is the maximum output of the kth hidden node during the training process, $a_k(t)$ is the minimum output of the kth hidden node during the training process.

③ Tune the structure of the recurrent self-organizing neural network

Pruning Step: If the total sensitivity index $ST_k(t)<\alpha_1$, $\alpha_1\in(0, 0.01]$, the kth hidden node will be pruned, the number of hidden nodes is updated, and $K_1=K-1$. Otherwise, the kth hidden node will not be pruned, and $K_1=K$.

Growing Step: if the current root-mean-squared error $E(t)>E_d$, a new hidden node will be added to the hidden layer of the recurrent self-organizing neural network, and the initial weights of the new hidden node are given by:

$$w_{new}^1(t) = w_h^1(t) = [w_{1h}^1(t), w_{2h}^1(t), \ldots, w_{5h}^1(t)], \tag{9}$$

$$w_{new}^2(t) = w_h^2(t),$$

$$w_{new}^3(t) = \frac{y_d(t) - y(t)}{v_{new}(t)},$$

$w_{new}^1(t)$ is the connecting weight vector between the new hidden node and the input layer, $w_{new}^2(t)$ is the self-feedback weight of the new hidden node, $w_{new}^3(t)$ is the connecting weight between the new hidden node and the output layer, h is the node which has the largest total sensitivity index, $w_h^1(t)$ is the connecting weight vector between the hth hidden node and input layer before adding new hidden node, $w_h^2(t)$ is the self-feedback weight of the hth hidden node before adding new hidden node, and the output of new hidden node is defined as:

$$v_{new}(t) = f\left(\sum_{m=1}^{5} w_{mh}^1(t) u_m(t) + v_{new}^1(t)\right), \tag{10}$$

$$v_{new}^1(t) = w_h^2(t) v_h(t-1),$$

and the number of hidden nodes is updated, $K_2=K_1+1$.

Otherwise, the structure of the recurrent self-organizing neural network will not be adjusted, and $K_2=K_1$.

④ Update the weights

The adaptation strategies of weights is defined as:

$$w_k^1(t+1) = w_k^1(t) + \eta_1 \frac{\partial E(t)}{\partial w_k^1(t)}, \tag{11}$$

$$w_k^2(t+1) = w_k^2(t) + \eta_2 \frac{\partial E(t)}{\partial w_k^2(t)},$$

$$w_k^3(t+1) = w_k^3(t) + \eta_3 \frac{\partial E(t)}{\partial w_k^3(t)},$$

where k=1, 2, K$_2$; $w_k^1(t)=[w_{1k}^1(t), w_{2k}^2(t), \ldots, w_{5k}^1(t)]$, $\eta_1\epsilon(0, 0.1]$, $\eta_2\epsilon(0, 0.1]$ and $\eta_3\epsilon(0, 0.01]$ are respectively the learning rate of the connection weights between input layer and hidden layer, the learning rate of the self-feedback weight in hidden layer, and the learning rate of the connection weights between hidden layer and output layer.

⑤ Import the training sample x(t+1), and repeat the steps ②-④, then, stop the training process after all of the training samples are imported to the neural network.

(4) The testing samples are then set to the trained recurrent self-organizing neural network. The outputs of the recurrent self-organizing neural network is the predicting values of effluent ammonia-nitrogen concentration. Moreover, the program of this intelligent method has been designed based on the former analysis. The program environment of the proposed intelligent method consists of a Windows 8 64-bit operating system, a clock speed of 2.6 GHz and 4 GB of RAM. And the program is based on the Matlab 2010 under the operating system.

One aspect of the present invention is directed to a method for predicting the effluent ammonia-nitrogen concentration in wastewater based on a recurrent self-organizing neural network, which includes:

(1) providing training samples, each training sample including input variables as measured parameters of a wastewater and a measured effluent ammonia-nitrogen concentration of the wastewater;

(2) designing a topological structure of a recurrent self-organizing neural network having an input layer, a hidden layer and an output layer, wherein an initial structure of the recurrent self-organizing neural network is M-K-1, having M nodes in the input layer, K nodes in the hidden layer and 1 node in the output layer, where M>3 is a positive integer and represents the number of the input variables, K>2 is a positive integer;

wherein an input vector of the recurrent self-organizing neural network is $u(t)=[u_1(t), u_2(t), \ldots, u_M(t)]$ at time t, where $u_1(t)$ is the value of input variable 1, $u_2(t)$ is the value of input variable 2, and $u_M(t)$ is the value of input variable M, respectively, at time t;

the output, y(t), of the recurrent self-organizing neural network, which is the calculated value of the effluent ammonia-nitrogen concentration at time t, is expressed as:

$$y(t) = \sum_{k=1}^{K} w_k^3(t) v_k(t), \quad (1)$$

where $w_k^3(t)$ is connecting weight between kth node in the hidden layer and the node in the output layer at time t, where k=1, 2, . . . , K; and $v_k(t)$ is the output of kth node in the hidden layer at time t:

$$v_k(t) = f\left(\sum_{m=1}^{M} w_{mk}^1(t) u_m(t) + v_k^1(t)\right), \quad (2)$$

where $w_{mk}^1(t)$ is connecting weight between mth node in the input layer and kth node in the hidden layer at time t, m=1, 2, . . . , M; $v_k^1(t)$ is feedback value of kth node in the hidden layer at time t which can be expressed as:

$$v_k^1(t) = w_k^2(t) v_k(t-1), \quad (3)$$

where $w_k^2(t)$ is self-feedback weight of kth node in the hidden layer at time t, $v_k(t-1)$ is the output of kth node in the hidden layer at time t−1;

wherein a root-mean-squared error is defined as:

$$E(t) = \frac{1}{2T} \sum_{t=1}^{T} (y_d(t) - y(t))^2, \quad (4)$$

where $y_d(t)$ is the real value of the effluent ammonia-nitrogen concentration at time t and T is the number of training samples;

(3) training the recurrent self-organizing neural network,

① initializing the connecting weight between the nodes in the hidden layer and the node in the output layer, the self-feedback weight of the nodes in the hidden layer, and the connecting weight between the nodes in the input layer and the nodes in the hidden layer, $w_k^3(t)\epsilon(0, 1)$, $w_k^2(t)\epsilon(0, 1)$, and $w_{mk}^1(t)\epsilon(0, 1)$, m=1, 2, . . . , M, k=1, 2, . . . , K, and pre-setting an expected error value $E_d$, $E_d \epsilon(0, 0.01]$.

② calculating the total sensitivity of the nodes in the hidden layer, respectively, as follows:

$$ST_k(t) = \frac{\text{Var}_k[E(y(t) | v_k(t))]}{\text{Var}[y(t)]}, \text{ where} \quad (5)$$

$$\text{Var}_k[E(y(t) | v_k(t))] = 2(A_k)^2 + (B_k)^2, \quad (6)$$

$$\text{Var}(y(t)) = 2 \sum_{k=1}^{K} ((A_k)^2 + (B_k)^2),$$

k=1, 2, . . . , K; $A_k$ and $B_k$ are Fourier coefficients which are given by:

$$A_k = \frac{1}{2\pi} \int_{-\pi}^{\pi} \cos(\omega_k(t)s) ds, \quad (7)$$

$$B_k = \frac{1}{2\pi} \int_{-\pi}^{\pi} \sin(\omega_k(t)s) ds,$$

where the range of s is $[-\pi, \pi]$; $\omega_k(t)$ is the frequency of kth node in the hidden layer, $\omega_k(t)$ is determined by the output of kth node in the hidden layer as follows:

$$\omega_k(t) = \arcsin \frac{\pi}{b_k(t) - a_k(t)} \left(v_k(t) - \frac{b_k(t) + a_k(t)}{2}\right), \quad (8)$$

where $b_k(t)$ is the maximum output of the kth node in the hidden layer during the training process, $a_k(t)$ is the minimum output of the kth node in the hidden layer during the training process;

③ tuning the structure of the recurrent self-organizing neural network pruning step: if the total sensitivity $ST_k(t)<\alpha_1$, $\alpha_1\epsilon(0, 0.01]$, the kth node in the hidden layer will be pruned, the number of nodes in the hidden layer is updated, and $K_1=K-1$; otherwise, the kth node in the hidden layer will not be pruned, and $K_1=K$;

growing step: if the root-mean-squared error $E(t)>E_d$, a new node will be added to the hidden layer, and an initial weight of the new node added to the hidden layer is given by:

$$w_{new}^1(t) = w_h^1(t) = [w_{1h}^1(t), w_{2h}^1(t), \ldots, w_{5h}^1(t)], \quad (9)$$
$$w_{new}^2(t) = w_h^2(t),$$
$$w_{new}^3(t) = \frac{y_d(t) - y(t)}{v_{new}(t)},$$

where $w_{new}^1(t)$ is connecting weight vector between the new node added to the hidden layer and the input layer, $w_{new}^2(t)$ is self-feedback weight of the new node added to the hidden layer, $w_{new}^3(t)$ is connecting weight between the new node added to the hidden layer and the output layer, h node is the node in the hidden layer which has the largest total sensitivity, $w_h^1(t)$ is connecting weight vector between the hth node in the hidden layer and the input layer before adding the new node to the hidden layer, $w_h^2(t)$ is self-feedback weight of the hth node in the hidden layer before adding the new node to the hidden layer, and the output of the new node added to the hidden layer is defined as:

$$v_{new}(t) = f\left(\sum_{m=1}^{M} w_{mh}^1(t)u_m(t) + v_{new}^1(t)\right), \quad (10)$$
$$v_{new}^1(t) = w_h^2(t)v_h(t-1),$$

and the number of nodes in the hidden layer is updated, $K_2 = K_1 + 1$;

otherwise, the structure of the recurrent self-organizing neural network will not be adjusted, and $K_2 = K_1$;

④ updating the weights $w_k^1(t)$, $w_k^2(t)$ and $w_k^3(t)$ the adaptation strategies of weights is defined as:

$$w_k^1(t+1) = w_k^1(t) + \eta_1 \frac{\partial E(t)}{\partial w_k^1(t)}, \quad (11)$$
$$w_k^2(t+1) = w_k^2(t) + \eta_2 \frac{\partial E(t)}{\partial w_k^2(t)},$$
$$w_k^3(t+1) = w_k^3(t) + \eta_3 \frac{\partial E(t)}{\partial w_k^3(t)},$$

where $k=1, 2, \ldots, K_2$; $w_k^1(t)=[w_{1k}^1(t), w_{2k}^1(t), \ldots, w_{Mk}^1(t)]$, $\eta_1 \in (0, 0.1]$, $\eta_2 \in (0, 0.1]$ and $\eta_3 \in (0, 0.01]$ are respectively the learning rate of the connection weights between the input layer and the hidden layer, the learning rate of the self-feedback weight in the hidden layer, and the learning rate of the connection weights between the hidden layer and the output layer;

⑤ importing training sample $x(t+1)$, and repeating steps ②-④, then, stopping the training process after all of the training samples are imported to the recurrent self-organizing neural network so as to obtain a trained recurrent self-organizing neural network;

(4) providing the same input variables of a wastewater to be monitored as that of the training samples, and inputting the input variables of the wastewater to be monitored to the trained recurrent self-organizing neural network to carry out calculation, wherein the output of the trained recurrent self-organizing neural network is the predicted value of the effluent ammonia-nitrogen concentration of the wastewater to be monitored.

Another aspect of the present invention is directed to a method for online real-time monitoring effluent ammonia-nitrogen concentration in wastewater, which includes:

providing a trained recurrent self-organizing neural network;

real-time measuring parameters of the wastewater to be monitored, which are used as input variables of the trained recurrent self-organizing neural network;

inputting the input variables to the trained recurrent self-organizing neural network to carry out calculation, wherein the output of the trained recurrent self-organizing neural network is the predicted value of the effluent ammonia-nitrogen concentration of the wastewater to be monitored;

repeating the real-time measuring parameters step and the inputting the input variables step by real-time measuring the parameters of the wastewater to be monitored, and inputting the input variables to the trained recurrent self-organizing neural network to carry out calculation in a predetermined interval, so that predicted values of the effluent ammonia-nitrogen concentration of the wastewater to be monitored are obtained continuously with time;

wherein the trained recurrent self-organizing neural network is obtained by:

(1) providing training samples, each training sample including input variables as measured parameters of a wastewater and a measured effluent ammonia-nitrogen concentration of the wastewater;

(2) designing a topological structure of a recurrent self-organizing neural network having an input layer, a hidden layer and an output layer, wherein an initial structure of the recurrent self-organizing neural network is M-K-1, having M nodes in the input layer, K nodes in the hidden layer and 1 node in the output layer, where M>3 is a positive integer and represents the number of the input variables, K>2 is a positive integer;

wherein an input vector of the recurrent self-organizing neural network is $u(t)=[u_1(t), u_2(t), u_M(t)]$ at time t, where $u_1(t)$ is the value of input variable 1, $u_2(t)$ is the value of input variable 2, and $u_M(t)$ is the value of input variable M, respectively, at time t;

the output, $y(t)$, of the recurrent self-organizing neural network, which is the calculated value of the effluent ammonia-nitrogen concentration at time t, is expressed as:

$$y(t) = \sum_{k=1}^{K} w_k^3(t)v_k(t), \quad (1)$$

where $w_k^3(t)$ is connecting weight between kth node in the hidden layer and the node in the output layer at time t, where $k=1, 2, \ldots, K$; and $v_k(t)$ is the output of kth node in the hidden layer at time t:

$$v_k(t) = f\left(\sum_{m=1}^{M} w_{mk}^1(t)u_m(t) + v_k^1(t)\right), \quad (2)$$

where $w_{mk}^1(t)$ is connecting weight between mth node in the input layer and kth node in the hidden layer at time t, m=1, 2, ..., M; $v_k^1(t)$ is feedback value of kth node in the hidden layer at time t which can be expressed as:

$$v_k^1(t) = w_k^2(t) v_k(t-1), \quad (3)$$

where $w_k^2(t)$ is self-feedback weight of kth node in the hidden layer at time t, $v_k(t-1)$ is the output of kth node in the hidden layer at time t−1;

wherein a root-mean-squared error is defined as:

$$E(t) = \frac{1}{2T} \sum_{t=1}^{T} (y_d(t) - y(t))^2, \quad (4)$$

where $y_d(t)$ is the real value of the effluent ammonia-nitrogen concentration at time t and T is the number of training samples;

(3) training the recurrent self-organizing neural network,

① initializing the connecting weight between the nodes in the hidden layer and the node in the output layer, the self-feedback weight of the nodes in the hidden layer, and the connecting weight between the nodes in the input layer and the nodes in the hidden layer, $w_k^3(t) \in (0, 1)$, $w_k^2(t) \in (0, 1)$, and $w_{mk}^1(t) \in (0, 1)$, m=1, 2, ..., M, k=1, 2, ..., K, and pre-setting an expected error value $E_d$, $E_d \in (0, 0.01]$.

② calculating the total sensitivity of the nodes in the hidden layer, respectively, as follows:

$$ST_k(t) = \frac{\text{Var}_k[E(y(t)|v_k(t))]}{\text{Var}[y(t)]}, \quad (5)$$

where $$\text{Var}_k[E(y(t)|v_k(t))] = 2(A_k)^2 + (B_k)^2,$$

$$\text{Var}(y(t)) = 2 \sum_{k=1}^{K} ((A_k)^2 + (B_k)^2), \quad (6)$$

k=1, 2, ..., K; $A_k$ and $B_k$ are Fourier coefficients which are given by:

$$A_k = \frac{1}{2\pi} \int_{-\pi}^{\pi} \cos(\omega_k(t)s) ds, \quad (7)$$

$$B_k = \frac{1}{2\pi} \int_{-\pi}^{\pi} \sin(\omega_k(t)s) ds,$$

where the range of s is [−π, π]; $\omega_k(t)$ is the frequency of kth node in the hidden layer, $\omega_k(t)$ is determined by the output of kth node in the hidden layer as follows:

$$\omega_k(t) = \arcsin \frac{\pi}{b_k(t) - a_k(t)} \left( v_k(t) - \frac{b_k(t) + a_k(t)}{2} \right), \quad (8)$$

where $b_k(t)$ is the maximum output of the kth node in the hidden layer during the training process, $a_k(t)$ is the minimum output of the kth node in the hidden layer during the training process;

③ tuning the structure of the recurrent self-organizing neural network pruning step: if the total sensitivity $ST_k(t) < \alpha_1$, $\alpha_1 \in (0, 0.01]$, the kth node in the hidden layer will be pruned, the number of nodes in the hidden layer is updated, and $K_1 = K - 1$; otherwise, the kth node in the hidden layer will not be pruned, and $K_1 = K$;

growing step: if the root-mean-squared error $E(t) > E_d$, a new node will be added to the hidden layer, and an initial weight of the new node added to the hidden layer is given by:

$$w_{new}^1(t) = w_h^1(t) = [w_{1h}^1(t), w_{2h}^1(t), \ldots, w_{5h}^1(t)], \quad (9)$$

$$w_{new}^2(t) = w_h^2(t),$$

$$w_{new}^3(t) = \frac{y_d(t) - y(t)}{v_{new}(t)},$$

where $w_{new}^1(t)$ is connecting weight vector between the new node added to the hidden layer and the input layer, $w_{new}^2(t)$ is self-feedback weight of the new node added to the hidden layer, $w_{new}^3(t)$ is connecting weight between the new node added to the hidden layer and the output layer, h node is the node in the hidden layer which has the largest total sensitivity, $w_h^1(t)$ is connecting weight vector between the hth node in the hidden layer and the input layer before adding the new node to the hidden layer, $w_h^2(t)$ is self-feedback weight of the hth node in the hidden layer before adding the new node to the hidden layer, and the output of the new node added to the hidden layer is defined as:

$$v_{new}(t) = f\left( \sum_{m=1}^{M} w_{mh}^1(t) u_m(t) + v_{new}^1(t) \right), \quad (10)$$

$$v_{new}^1(t) = w_h^2(t) v_h(t-1),$$

and the number of nodes in the hidden layer is updated, $K_2 = K_1 + 1$;

otherwise, the structure of the recurrent self-organizing neural network will not be adjusted, and $K_2 = K_1$;

④ updating the weights $w_k^1(t)$, $w_k^2(t)$ and $w_k^3(t)$
the adaptation strategies of weights is defined as:

$$w_k^1(t+1) = w_k^1(t) + \eta_1 \frac{\partial E(t)}{\partial w_k^1(t)}, \quad (11)$$

$$w_k^2(t+1) = w_k^2(t) + \eta_2 \frac{\partial E(t)}{\partial w_k^2(t)},$$

$$w_k^3(t+1) = w_k^3(t) + \eta_3 \frac{\partial E(t)}{\partial w_k^3(t)},$$

where k=1, 2, ..., $K_2$; $w_k^1(t) = [w_{1k}^1(t), w_{2k}^1, \ldots w_{Mk}^1(t)]$, $\eta_1 \in (0, 0.1]$, $\eta_2 \in (0, 0.1]$ and $\eta_3 \in (0, 0.01]$ are respectively the learning rate of the connection weights between the input layer and the hidden layer, the learning rate of the self-feedback weight in the hidden layer, and the learning rate of the connection weights between the hidden layer and the output layer;

⑤ importing training sample x(t+1), and repeating steps ②-④, then, stopping the training process after all of the training samples are imported to the recurrent self-organizing neural network so as to obtain the trained recurrent self-organizing neural network.

The novelties of this patent contain:

(1) In order to measure the effluent ammonia-nitrogen concentration online, an intelligent method is developed in this invention. The results demonstrate that the effluent ammonia-nitrogen concentration trends in urban WWTP can be predicted with acceptable accuracy using the TP, ORP, DO, TSS, and the effluent pH data as input variables. This proposed intelligent method can predict the effluent ammonia-nitrogen concentration with acceptable accuracy and solve the problem that the effluent ammonia-nitrogen concentration is difficult to be measured online.

(2) This intelligent method is based on the recurrent self-organizing neural network in this patent, which is able to optimize both the parameters and the network size during the learning process simultaneously. The advantages of the proposed recurrent self-organizing neural network are that it can simplify and accelerate the structure optimization process of the neural network, and can predict the effluent ammonia-nitrogen concentration accurately. Moreover, the predicting performance shows that the recurrent self-organizing neural network-based intelligent method can match system nonlinear dynamics. Therefore, this intelligent method performs well in the whole operating space.

Attention: an embodiment of this invention utilizes five input variables in this intelligent method to predict the effluent ammonia-nitrogen concentration. In fact, it is in the scope of this patent that any of the variables: the TP, ORP, DO, TSS, and the effluent pH, are used to predict the effluent ammonia-nitrogen concentration. Moreover, this intelligent method is also able to predict the others variables in urban WWTP.

Figure 1:
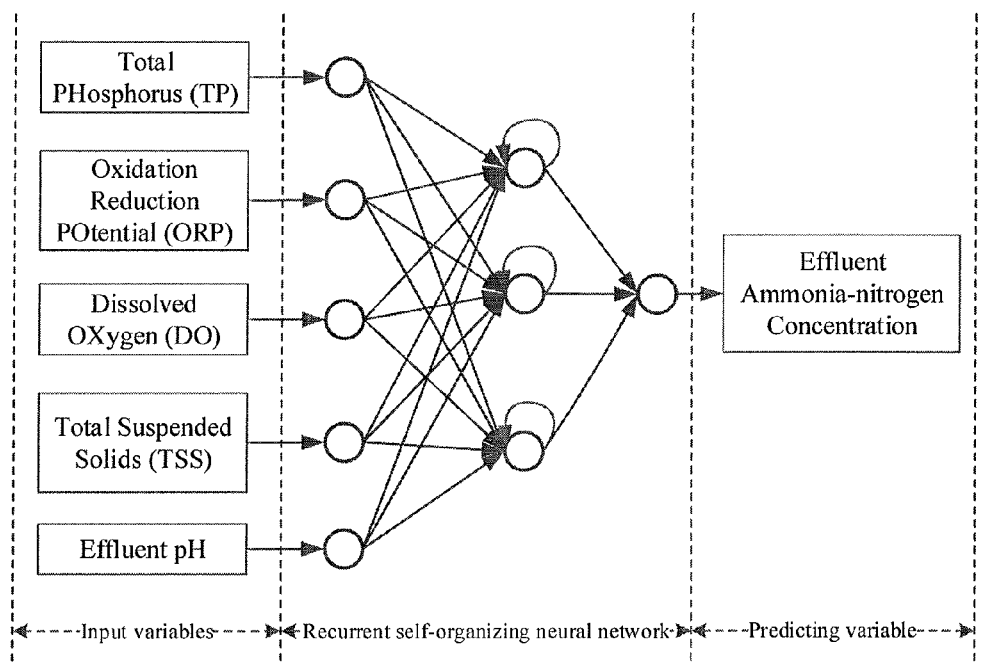
FIG. 1 shows the overall flow chart of the intelligent method for predicting effluent ammonia-nitrogen concentration in this patent.

Tables 1-14 show the experimental data in this invention. Tables 1-6 show the training samples of the TP, ORP, DO, TSS, the effluent pH and the real effluent ammonia-nitrogen concentration. Table 7 shows the outputs of the intelligent method in the training process. Tables 8-13 show the testing samples of the TP, ORP, DO, TSS, the effluent pH and real effluent ammonia-nitrogen concentration. Table 14 shows the outputs of the intelligent method in the predicting process. Moreover, the samples are imported as the sequence from the tables. The first data is in the first row and the first column. Then, the second data is in the first row and the second column. Until all of data is imported from the first row, the data in the second row and following rows are inputted as the same way.

DETAILED DESCRIPTION OF EMBODIMENTS

One aspect of the present invention is directed to a method for predicting the effluent ammonia-nitrogen concentration in wastewater based on a recurrent self-organizing neural network, which includes:

(1) providing training samples, each training sample including input variables as measured parameters of a wastewater and a measured effluent ammonia-nitrogen concentration of the wastewater;

(2) designing a topological structure of a recurrent self-organizing neural network having an input layer, a hidden layer and an output layer, wherein an initial structure of the recurrent self-organizing neural network is M-K-1, having M nodes in the input layer, K nodes in the hidden layer and 1 node in the output layer, where M>3 is a positive integer and represents the number of the input variables, K>2 is a positive integer;

wherein an input vector of the recurrent self-organizing neural network is $u(t)=[u_1(t), u_2(t), u_M(t)]$ at time t, where $u_1(t)$ is the value of input variable 1, $u_2(t)$ is the value of input variable 2, and $u_M(t)$ is the value of input variable M, respectively, at time t;

the output, $y(t)$, of the recurrent self-organizing neural network, which is the calculated value of the effluent ammonia-nitrogen concentration at time t, is expressed as:

$$y(t) = \sum_{k=1}^{K} w_k^3(t) v_k(t), \quad (1)$$

where $w_k^3(t)$ is connecting weight between kth node in the hidden layer and the node in the output layer at time t, where k=1, 2, . . . , K; and $v_k(t)$ is the output of kth node in the hidden layer at time t:

$$v_k(t) = f\left(\sum_{m=1}^{M} w_{mk}^1(t) u_m(t) + v_k^1(t)\right), \quad (2)$$

where $w_{mk}^1(t)$ is connecting weight between mth node in the input layer and kth node in the hidden layer at time t, m=1, 2, . . . , M; $v_k^1(t)$ is feedback value of kth node in the hidden layer at time t which can be expressed as:

$$v_k^1(t) = w_k^2(t) v_k(t-1), \quad (3)$$

where $w_k^2(t)$ is self-feedback weight of kth node in the hidden layer at time t, $v_k(t-1)$ is the output of kth node in the hidden layer at time t-1;

wherein a root-mean-squared error is defined as:

$$E(t) = \frac{1}{2T} \sum_{t=1}^{T} (y_d(t) - y(t))^2, \quad (4)$$

where $y_d(t)$ is the real value of the effluent ammonia-nitrogen concentration at time t and T is the number of training samples;

(3) training the recurrent self-organizing neural network,

① initializing the connecting weight between the nodes in the hidden layer and the node in the output layer, the self-feedback weight of the nodes in the hidden layer, and the connecting weight between the nodes in the input layer and the nodes in the hidden layer, $w_k^3(t) \in (0, 1)$, $w_k^2(t) \in (0, 1)$, and $w_{mk}^1(t) \in (0, 1)$, m=1, 2, . . . , M, k=1, 2, . . . , K, and pre-setting an expected error value $E_d$, $E_d \in (0, 0.01]$.

② calculating the total sensitivity of the nodes in the hidden layer, respectively, as follows:

$$ST_k(t) = \frac{\text{Var}_k[E(y(t) \mid v_k(t))]}{\text{Var}[y(t)]}, \quad (5)$$

where $$\text{Var}_k[E(y(t) \mid v_k(t))] = 2(A_k)^2 + (B_k)^2, \quad (6)$$

$$\text{Var}(y(t)) = 2 \sum_{k=1}^{K} ((A_k)^2 + (B_k)^2),$$

k=1, 2, ..., K; $A_k$ and $B_k$ are Fourier coefficients which are given by:

$$A_k = \frac{1}{2\pi}\int_{-\pi}^{\pi} \cos(\omega_k(t)s)ds, \quad (7)$$

$$B_k = \frac{1}{2\pi}\int_{-\pi}^{\pi} \sin(\omega_k(t)s)ds,$$

where the range of s is $[-\pi, \pi]$; $\omega_k(t)$ is the frequency of kth node in the hidden layer, $\omega_k(t)$ is determined by the output of kth node in the hidden layer as follows:

$$\omega_k(t) = \arcsin\frac{\pi}{b_k(t)-a_k(t)}\left(v_k(t) - \frac{b_k(t)+a_k(t)}{2}\right), \quad (8)$$

where $b_k(t)$ is the maximum output of the kth node in the hidden layer during the training process, $a_k(t)$ is the minimum output of the kth node in the hidden layer during the training process;

③ tuning the structure of the recurrent self-organizing neural network pruning step: if the total sensitivity $ST_k(t) < \alpha_1$, $\alpha_1 \in (0, 0.01]$, the kth node in the hidden layer will be pruned, the number of nodes in the hidden layer is updated, and $K_1 = K-1$; otherwise, the kth node in the hidden layer will not be pruned, and $K_1 = K$;

growing step: if the root-mean-squared error $E(t) > E_d$, a new node will be added to the hidden layer, and an initial weight of the new node added to the hidden layer is given by:

$$w_{new}^1(t) = w_h^1(t) = [w_{1h}^1(t), w_{2h}^1(t), \ldots, w_{5h}^1(t)], \quad (9)$$

$$w_{new}^2(t) = w_h^2(t),$$

$$w_{new}^3(t) = \frac{y_d(t) - y(t)}{v_{new}(t)},$$

where $w_{new}^1(t)$ is connecting weight vector between the new node added to the hidden layer and the input layer, $w_{new}^2(t)$ is self-feedback weight of the new node added to the hidden layer, $w_{new}^3(t)$ is connecting weight between the new node added to the hidden layer and the output layer, h node is the node in the hidden layer which has the largest total sensitivity, $w_h^1(t)$ is connecting weight vector between the hth node in the hidden layer and the input layer before adding the new node to the hidden layer, $w_h^2(t)$ is self-feedback weight of the hth node in the hidden layer before adding the new node to the hidden layer, and the output of the new node added to the hidden layer is defined as:

$$v_{new}(t) = f\left(\sum_{m=1}^{M} w_{mh}^1(t)u_m(t) + v_{new}^1(t)\right), \quad (10)$$

$$v_{new}^1(t) = w_h^2(t)v_h(t-1),$$

and the number of nodes in the hidden layer is updated, $K_2 = K_1 + 1$;

otherwise, the structure of the recurrent self-organizing neural network will not be adjusted, and $K_2 = K_1$;

④ updating the weights $w_k^1(t)$, $w_k^2(t)$ and $w_k^3(t)$ the adaptation strategies of weights is defined as:

$$w_k^1(t+1) = w_k^1(t) + \eta_1 \frac{\partial E(t)}{\partial w_k^1(t)}, \quad (11)$$

$$w_k^2(t+1) = w_k^2(t) + \eta_2 \frac{\partial E(t)}{\partial w_k^2(t)},$$

$$w_k^3(t+1) = w_k^3(t) + \eta_3 \frac{\partial E(t)}{\partial w_k^3(t)},$$

where k=1, 2, ..., $K_2$; $w_k^1(t) = [w_{1k}^1(t), w_{2k}^1(t), \ldots, w_{Mk}^1(t)]$, $\eta_1 \in (0, 0.1]$, $\eta_2 \in (0, 0.1]$ and $\eta_3 \in (0, 0.01]$ are respectively the learning rate of the connection weights between the input layer and the hidden layer, the learning rate of the self-feedback weight in the hidden layer, and the learning rate of the connection weights between the hidden layer and the output layer;

⑤ importing training sample x(t+1), and repeating steps ②-④, then, stopping the training process after all of the training samples are imported to the recurrent self-organizing neural network so as to obtain a trained recurrent self-organizing neural network;

(4) providing the same input variables of a wastewater to be monitored as that of the training samples, and inputting the input variables of the wastewater to be monitored to the trained recurrent self-organizing neural network to carry out calculation, wherein the output of the trained recurrent self-organizing neural network is the predicted value of the effluent ammonia-nitrogen concentration of the wastewater to be monitored.

In the above method for predicting effluent ammonia-nitrogen concentration in wastewater, the input variables of the recurrent self-organizing neural network are parameters measured in the wastewater, and various parameters can be selected as the input variables. For example, the number of the input variables, M, can be in the range of 4-8, and the input variables may include total phosphorus (TP), oxidation reduction potential (ORP), dissolved oxygen (DO), total suspended solids (TSS), effluent pH, temperature, influent rate, and sludge volume index (SVI) of the wastewater. TP is used to measure the existing total phosphorus in inorganic and organic state. ORP reflects the macroscopic oxidation-reduction of all substances in aqueous. DO represents percentage of the oxygen saturation concentration. TSS is used to detect the suspensions in wastewater. pH measures the acidity or alkalinity of the wastewater. Temperature is used to detect the temperature values in wastewater. Influent rate reflects the influent wastewater rate of the wastewater, and SVI measures the sludge bulking values of the wastewater.

In an embodiment, the number of the input variables, M, is 5, and the input variables are the total phosphorus (TP), the oxidation reduction potential (ORP), the dissolved oxygen (DO), the total suspended solids (TSS), and the effluent pH of the wastewater. These parameters can be measured according to any conventional method in the field.

In the above method for predicting effluent ammonia-nitrogen concentration in wastewater, once a trained recurrent self-organizing neural network is obtained, step (4) can be repeated in a predetermined interval, for example every 5-30 minutes, by providing real-time measured input variables of the wastewater to be monitored, and inputting the input variables to the trained recurrent self-organizing neural network to carry out calculation, so that predicted values of the effluent ammonia-nitrogen concentration of the wastewater to be monitored are obtained continuously with time. The time delay from real-time measuring an input variable to input the measured input variable into the trained recurrent self-organizing neural network and obtain the calculated result of the effluent ammonia-nitrogen concentration in the wastewater is neglectable. In this way, real-time monitoring of the effluent ammonia-nitrogen concentration in wastewater is realized.

In the method for predicting effluent ammonia-nitrogen concentration in wastewater, the number of the training samples used for training the recurrent self-organizing neural network can be selected as long as a reasonably accurate trained recurrent self-organizing neural network is obtained. For example, the number of training samples can be in the range of 100-300.

In the above method for predicting effluent ammonia-nitrogen concentration in wastewater, the training samples may be taken from the wastewater to be monitored or from other wastewater with similar properties as that of the wastewater to be monitored. The training samples may historic data, or obtained online from the wastewater being monitored when monitoring the wastewater.

The above method for predicting effluent ammonia-nitrogen concentration in wastewater may further include online training the recurrent self-organizing neural network using training samples taken from the wastewater to be monitored in the process of calculating the effluent ammonia-nitrogen concentration in the wastewater to be monitored.

Another aspect of the present invention is directed to a method for online real-time monitoring effluent ammonia-nitrogen concentration in wastewater, which includes:

providing a trained recurrent self-organizing neural network;

real-time measuring parameters of the wastewater to be monitored, which are used as input variables of the trained recurrent self-organizing neural network;

inputting the input variables to the trained recurrent self-organizing neural network to carry out calculation, wherein the output of the trained recurrent self-organizing neural network is the predicted value of the effluent ammonia-nitrogen concentration of the wastewater to be monitored;

repeating the real-time measuring parameters step and the inputting the input variables step by real-time measuring the parameters of the wastewater to be monitored, and inputting the input variables to the trained recurrent self-organizing neural network to carry out calculation in a predetermined interval, so that predicted values of the effluent ammonia-nitrogen concentration of the wastewater to be monitored are obtained continuously with time;

wherein the trained recurrent self-organizing neural network can be obtained by any method described above and throughout this disclosure.

In the above method for predicting effluent ammonia-nitrogen concentration in wastewater, the inputting input variables step can be repeated in a predetermined interval, for example every 0.5-5 min, by using corresponding real-time measured parameters of the wastewater as input variables.

In practice, parameters of the wastewater in a wastewater treatment process can be measured continuously by inserting one or more probes into the wastewater at proper positions, the obtained signals are processed and input into the recurrent self-organizing neural network. This process can be carried out by a computer controlled system. Such a computer controlled system may include a data acquisition unit for real-time collecting and processing wastewater sample to obtain the time dependent values of the input variables and a calculation unit for conduct the calculation based on the input variables. The whole process of sampling the wastewater, obtaining values of measured parameters, inputting the measured parameters as input variables, and obtaining the calculation result of the effluent ammonia-nitrogen concentration usually takes less than 1 min.

The above method for predicting effluent ammonia-nitrogen concentration may further comprise online retraining the trained recurrent self-organizing neural network by using training samples taken from the wastewater to be monitored in the process of predicting the effluent ammonia-nitrogen concentration in the wastewater to be monitored. In such retraining process, the corresponding real effluent ammonia-nitrogen concentration of the wastewater needs to be measured or is otherwise known.

An intelligent method is developed to predict the effluent ammonia-nitrogen concentration based on a recurrent self-organizing neural network in this patent. For this intelligent method, the inputs are those variables that are easy to measure and the outputs are estimates of the effluent ammonia-nitrogen concentration. For this patent, an experimental scheme is set up as shown in FIG. 1. The historical process data are routinely acquired and stored in the data acquisition system. The data can be easily retrieved. The variables whose data are easy to measure by the instruments include: the TP, ORP, DO, TSS, and the effluent pH according to an embodiment.

This proposed patent adopts the following technical scheme and implementation steps:

An intelligent method for the effluent ammonia-nitrogen concentration based on a recurrent self-organizing neural network, its characteristic and steps include the following steps:

(1) Select input variables

Learning from the work experience in operating urban WWTP and our analysis of its detailed mechanism, a total of five process variables have been chosen as the input variables to develop the intelligent method: the TP, ORP, DO, TSS, and the effluent pH, respectively.

The experimental data is obtained from an urban WWTP in 2014. There are 245 groups of samples which are divided into two parts: 165 groups of training samples and 80 groups of testing samples.

(2) Design the recurrent self-organizing neural network

The recurrent self-organizing neural network consists of three layers: input layer, hidden layer and output layer. The initial structure is 5-K-1. There are 5 nodes in the input layer, K nodes in the hidden layer and 1 node in the output layer, K=3. The number of training samples is T=165. The input vector of the recurrent self-organizing neural network is $u(t)=[u_1(t), u_2(t), u_3(t), u_4(t), u_5(t)]$ at time t. $u_1(t)$ is the value of TP, $u_2(t)$ is the value of ORP, $u_3(t)$ is the value of DO, $u_4(t)$ is the value of TSS, and $u_5(t)$ is the value of effluent pH at time t respectively. $y(t)$ is the output of the recurrent self-organizing neural network, and $y_d(t)$ is the real value of the effluent ammonia-nitrogen concentration at time t respectively. The output of the recurrent self-organizing neural network can be described:

$$y(t) = \sum_{k=1}^{K} w_k^3(t) v_k(t), \quad (12)$$

where $w_k^3(t)$ is the connecting weight between the kth hidden node and the output node at time t, k=1, 2, . . . , K; and $v_k(t)$ is the output of the kth hidden layer at time t:

$$v_k(t) = f\left(\sum_{m=1}^{5} w_{mk}^1(t)u_m(t) + v_k^1(t)\right), \quad (13)$$

$w_{mk}^1(t)$ is the connecting weight between the mth node in the input layer and the kth hidden node at time t, m=1, 2, . . . , 5; $v_k^1(t)$ is the feedback value of the kth hidden node at time t which can be described as:

$$v_k^1(t) = w_k^2(t)v_k(t-1), \quad (14)$$

$w_k^2(t)$ is the self-feedback weight of the kth hidden node at time t, $v_k(t-1)$ is the output of the kth hidden layer at time t−1;

Moreover, the root-mean-squared error is defined:

$$E(t) = \frac{1}{2T}\sum_{t=1}^{T}(y_d(t) - y(t))^2, \quad (15)$$

where T=165 is the number of the training samples.

(3) Train the recurrent self-organizing neural network

① Initialize the connecting weights between the hidden nodes and the output node, the self-feedback weights of the hidden nodes, and the connecting weights between the nodes in the input layer and the hidden nodes, $w_k^3(t)\in(0, 1)$, $w_k^2(t)\in(0, 1)$, and $w_{mk}^1(t)\in(0, 1)$, m=1, 2, . . . , 5, k=1, 2, . . . , K, pre-set the expected error value $E_d$=0.01.

② Calculate the sensitivity of hidden nodes:

$$ST_k(t) = \frac{\text{Var}_k[E(y(t)|v_k(t))]}{\text{Var}[y(t)]}, \quad (16)$$

where $$\text{Var}_k[E(y(t)|v_k(t))] = 2(A_k)^2 + (B_k)^2,$$

$$\text{Var}(y(t)) = 2\sum_{k=1}^{K}((A_k)^2 + (B_k)^2), \quad (17)$$

k=1, 2, . . . , K; $A_k$ and $B_k$ are the Fourier coefficients which are given by:

$$A_k = \frac{1}{2\pi}\int_{-\pi}^{\pi}\cos(\omega_k(t)s)ds, \quad (18)$$

$$B_k = \frac{1}{2\pi}\int_{-\pi}^{\pi}\sin(\omega_k(t)s)ds,$$

where the range of s is $[-\pi, \pi]$; $\omega_k(t)$ is the frequency of the kth hidden node, $\omega_k(t)$ is decided by the output of the kth hidden node:

$$\omega_k(t) = \arcsin\frac{\pi}{b_k(t) - a_k(t)}\left(v_k(t) - \frac{b_k(t) + a_k(t)}{2}\right), \quad (19)$$

where $b_k(t)$ is the maximum output of the kth hidden node during the training process, $a_k(t)$ is the minimum output of the kth hidden node during the training process.

③ Tune the structure of the recurrent self-organizing neural network

Pruning Step: If the total sensitivity index $ST_k(t)<\alpha_1$, $\alpha_1$=0.01, the kth hidden node will be pruned, the number of hidden nodes is updated, and $K_1$=K−1. Otherwise, the kth hidden node will not be pruned, and $K_1$=K.

Growing Step: if the current root-mean-squared error $E(t)>E_d$, a new hidden node will be added to the hidden layer of the recurrent self-organizing neural network, and the initial weights of the new hidden node are given by:

$$w_{new}^1(t) = w_h^1(t) = [w_{1h}^1(t), w_{2h}^1(t), \ldots, w_{5h}^1(t)], \quad (20)$$

$$w_{new}^2(t) = w_h^2(t),$$

$$w_{new}^3(t) = \frac{y_d(t) - y(t)}{v_{new}(t)},$$

$w_{new}^1(t)$ is the connecting weight vector between the new hidden node and the input layer, $w_{new}^2(t)$ is the self-feedback weight of the new hidden node, $w_{new}^3(t)$ is the connecting weight between the new hidden node and the output layer, h is the node which has the largest total sensitivity index, $w_h^1(t)$ is the connecting weight vector between the hth hidden node and input layer before adding new hidden node, $w_h^2(t)$ is the self-feedback weight of the hth hidden node before adding new hidden node, and the output of new hidden node is defined as:

$$v_{new}(t) = f\left(\sum_{m=1}^{5}w_{mh}^1(t)u_m(t) + v_{new}^1(t)\right), \quad (21)$$

$$v_{new}^1(t) = w_h^2(t)v_h(t-1),$$

and the number of hidden nodes is updated, $K_2=K_1+1$.

Otherwise, the structure of the recurrent self-organizing neural network will not be adjusted, and $K_2=K_1$.

④ Update the weights

The adaptation strategies of weights is defined as:

$$w_k^1(t+1) = w_k^1(t) + \eta_1\frac{\partial E(t)}{\partial w_k^1(t)}, \quad (22)$$

$$w_k^2(t+1) = w_k^2(t) + \eta_2\frac{\partial E(t)}{\partial w_k^2(t)},$$

$$w_k^3(t+1) = w_k^3(t) + \eta_3\frac{\partial E(t)}{\partial w_k^3(t)},$$

where k=1, 2, . . . , $K_2$; $w_k^1(t)=[w_{1k}^1(t), w_{2k}^1(t), \ldots, w_{5k}^1(t)]$, $\eta_1$=0.01, $\eta_2$=0.01 and $\eta_3$=0.001 are respectively the learning rate of the connection weights between input layer and hidden layer, the learning rate of the self-feedback weight in hidden layer, and the learning rate of the connection weights between hidden layer and output layer.

⑤ Import the training sample x(t+1), and repeat the steps ②-④, then, stop the training process after all of the training samples are imported to the neural network.

Figure 2:
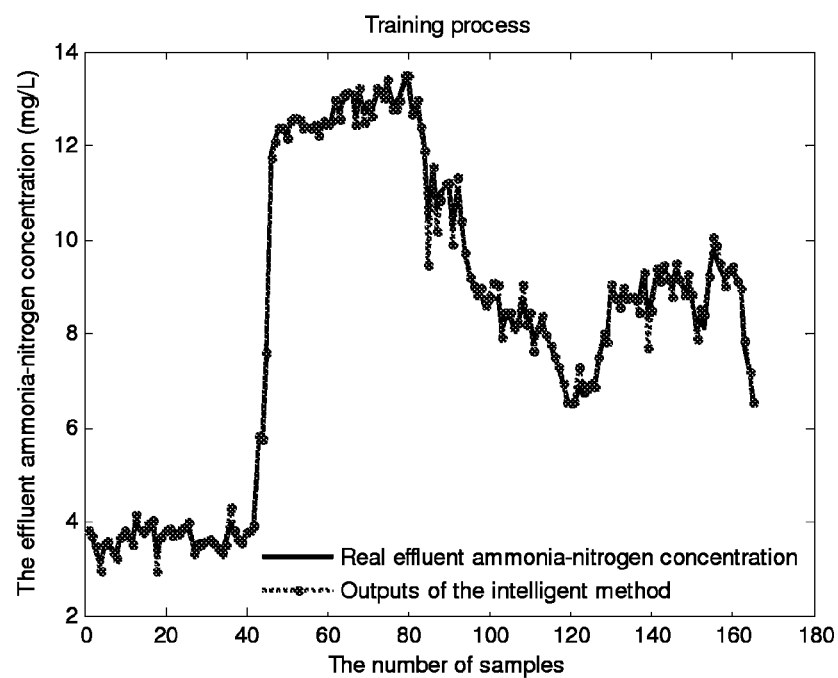
FIG. 2 shows the training result of the intelligent method.
Figure 3:
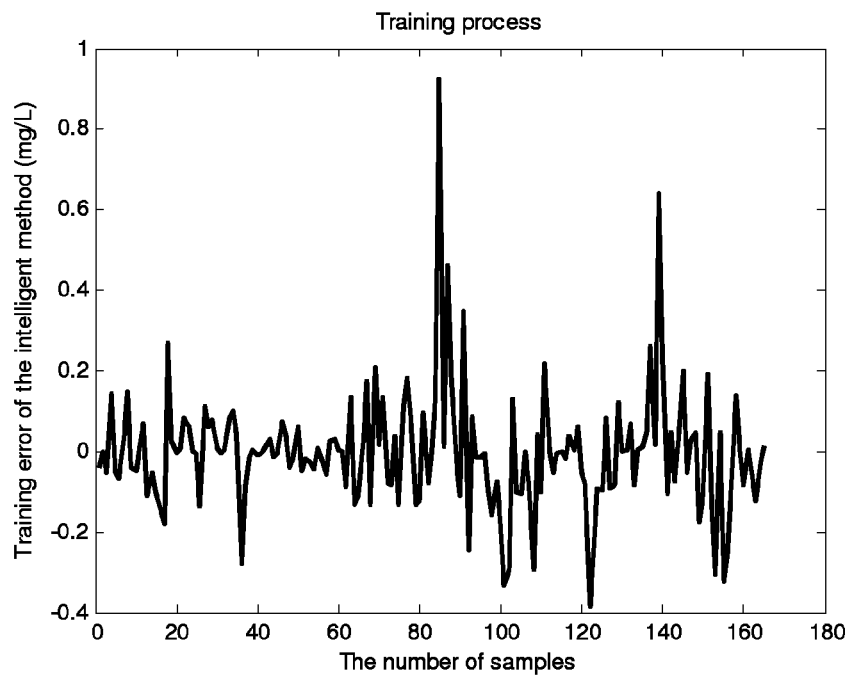
FIG. 3 shows the training error of the intelligent method.

The training results of the intelligent method are shown in FIG. 2. X axis shows the number of samples. Y axis shows the effluent ammonia-nitrogen concentration. The unit of Y axis is mg/L. The solid line presents the real values of effluent ammonia-nitrogen concentration. The dotted line shows the outputs of intelligent method in the training process. The errors between the real values and the outputs of intelligent method in the training process are shown in FIG. 3. X axis shows the number of samples. Y axis shows the training error. The unit of Y axis is mg/L.

Figure 4:
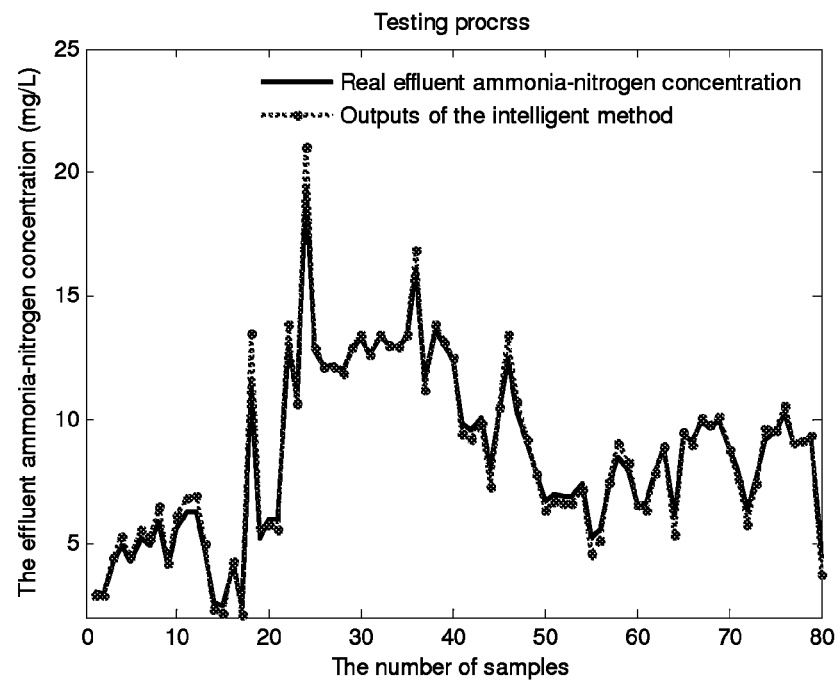
FIG. 4 shows the predicting result of the intelligent method.
Figure 5:
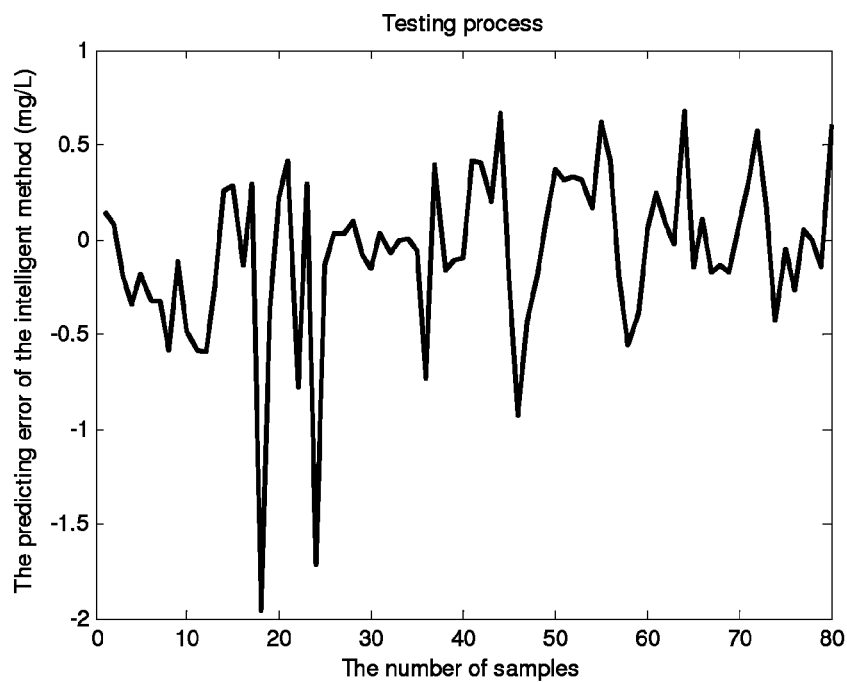
FIG. 5 shows the predicting error of the intelligent method.

(4) The testing samples are then set to the trained recurrent self-organizing neural network. The outputs of the recurrent self-organizing neural network are the predicting values of effluent ammonia-nitrogen concentration. The predicting results are shown in FIG. 4. X axis shows the number of samples. Y axis shows the effluent ammonia-nitrogen concentration. The unit of Y axis is mg/L. The solid line presents the real values of effluent ammonia-nitrogen concentration. The dotted line shows the outputs of intelligent method in the testing process. The errors between the real values and the outputs of intelligent method in the testing process are shown in FIG. 5. X axis shows the number of samples. Y axis shows the testing error. The unit of Y axis is mg/L.

TABLE 1

The training samples of TP (mg/L)

| | | | | | | | | | |
|---|---|---|---|---|---|---|---|---|---|
| 3.9021 | 3.8943 | 4.3182 | 4.2219 | 4.6025 | 4.3496 | 4.5057 | 4.5057 | 4.5057 | 4.5057 |
| 3.8848 | 3.8155 | 3.9287 | 4.0154 | 4.1802 | 4.1465 | 4.1465 | 4.1465 | 4.1465 | 4.1465 |
| 4.1465 | 4.1465 | 4.2845 | 3.8326 | 3.7941 | 4.4504 | 4.3140 | 4.4706 | 4.2410 | 4.5929 |
| 4.4944 | 3.8420 | 3.8664 | 4.0551 | 4.2081 | 4.1305 | 4.2712 | 3.5370 | 2.8337 | 4.1774 |
| 3.7040 | 3.6206 | 4.1277 | 4.0534 | 4.3345 | 4.1899 | 4.3530 | 4.2267 | 4.1365 | 4.0805 |
| 4.0221 | 3.9322 | 3.8749 | 4.0820 | 4.0727 | 4.1665 | 4.2180 | 4.1436 | 4.3808 | 4.4049 |
| 4.2351 | 4.2345 | 4.1325 | 3.9768 | 3.9608 | 3.7857 | 3.8670 | 3.8294 | 3.9176 | 4.0762 |
| 4.0099 | 4.1032 | 4.0226 | 4.0941 | 4.1105 | 4.1284 | 4.0332 | 4.0053 | 3.9005 | 3.8975 |
| 3.7953 | 3.8648 | 3.8835 | 3.9725 | 4.2412 | 4.4562 | 4.2018 | 4.1647 | 4.5131 | 4.1541 |
| 4.0418 | 4.0789 | 3.9439 | 3.7140 | 3.9232 | 4.0274 | 3.9716 | 4.0438 | 4.2394 | 4.2394 |
| 4.2394 | 4.2394 | 4.2394 | 4.2394 | 4.2394 | 4.2394 | 4.2394 | 4.2392 | 4.2392 | 4.2392 |
| 4.2392 | 4.2392 | 4.2392 | 4.2392 | 3.6244 | 4.2873 | 4.0612 | 3.9821 | 4.0342 | 4.0920 |
| 4.0371 | 4.0575 | 4.1273 | 4.1907 | 4.2153 | 4.2907 | 4.1859 | 4.1446 | 4.0744 | 4.3648 |
| 3.8792 | 3.7862 | 3.8169 | 3.7380 | 3.8215 | 4.0155 | 4.0076 | 3.9549 | 4.0678 | 4.0160 |
| 3.9320 | 4.0386 | 3.9331 | 3.8880 | 3.7802 | 3.6751 | 3.6112 | 3.6098 | 3.6671 | 3.6269 |
| 3.7581 | 3.8980 | 4.0578 | 3.9783 | 3.9331 | 3.9794 | 4.0795 | 4.1422 | 4.7669 | 4.3334 |
| 4.4615 | 4.1052 | 4.0354 | 4.0672 | 4.2935 | | | | | |

TABLE 2

The training samples of ORP

| | | | | | | | | | |
|---|---|---|---|---|---|---|---|---|---|
| 540.2970 | 546.8350 | 554.3970 | 556.1280 | 553.4360 | 551.0650 | 549.9110 | 554.5260 | 556.3200 | 561.1910 |
| 555.0380 | 548.5010 | 550.9370 | 563.9470 | 564.7160 | 565.5500 | 565.2290 | 565.1010 | 563.7550 | 564.7160 |
| 564.7800 | 565.6140 | 565.6140 | 564.6520 | 563.8830 | 566.1260 | 565.5500 | 565.2290 | 564.8440 | 470.6930 |
| 480.6910 | 414.3560 | 539.2080 | 555.3590 | 557.9870 | 558.8200 | 558.9480 | 526.9660 | 470.4370 | 567.4720 |
| 565.1650 | 563.8190 | 578.6880 | 581.2520 | 581.2520 | 582.1490 | 581.8290 | 581.7650 | 581.7650 | 581.2520 |
| 580.9960 | 580.4830 | 579.8420 | 579.7140 | 579.7780 | 580.4190 | 580.7390 | 580.5470 | 580.7390 | 580.4830 |
| 580.0980 | 580.0340 | 579.0730 | 578.6240 | 578.2400 | 578.3040 | 576.9580 | 577.4070 | 577.9830 | 578.2400 |
| 578.1760 | 577.8550 | 577.7270 | 577.4710 | 577.2780 | 577.0860 | 576.8940 | 576.8940 | 577.4070 | 575.0350 |
| 572.9840 | 573.7530 | 574.9070 | 574.7790 | 575.0990 | 575.2270 | 573.8170 | 572.2150 | 572.6640 | 573.0480 |
| 572.4070 | 572.0230 | 571.4460 | 573.9460 | 573.8170 | 573.9460 | 574.2660 | 574.9070 | 575.7400 | 575.7400 |
| 575.0990 | 575.0350 | 574.5860 | 574.1380 | 573.9460 | 573.6890 | 573.3050 | 575.0350 | 574.8430 | 574.1380 |
| 574.0100 | 573.6890 | 573.7530 | 572.0230 | 570.9970 | 570.1000 | 569.9720 | 570.7410 | 571.7020 | 572.1510 |
| 572.1510 | 572.6640 | 573.2410 | 573.3690 | 573.1760 | 573.1120 | 573.0480 | 573.0480 | 573.1120 | 573.1760 |
| 574.5860 | 578.3680 | 578.7530 | 577.2780 | 573.2410 | 570.4210 | 570.9330 | 572.0870 | 572.1510 | 570.2920 |
| 570.0360 | 568.7540 | 567.0240 | 568.4340 | 569.0100 | 568.8820 | 568.9460 | 569.2670 | 569.4590 | 569.5230 |
| 570.1000 | 571.5100 | 572.4070 | 572.8560 | 572.1510 | 570.6770 | 570.3560 | 569.9720 | 569.6510 | 569.5870 |
| 569.7150 | 570.1640 | 570.8690 | 570.9330 | 571.5740 | | | | | |

TABLE 3

The training samples of DO (mg/L)

| | | | | | | | | | |
|---|---|---|---|---|---|---|---|---|---|
| 0.0518 | 0.0394 | 0.0379 | 0.0356 | 0.0370 | 0.0361 | 0.0467 | 0.0417 | 0.0510 | 0.0382 |
| 0.0411 | 0.0363 | 0.0472 | 0.0581 | 0.0514 | 0.0561 | 0.0673 | 0.0585 | 0.0507 | 0.0486 |
| 0.0484 | 0.0492 | 0.1343 | 0.0793 | 0.0561 | 0.0696 | 0.0427 | 0.0441 | 0.0480 | 0.0571 |
| 0.0464 | 0.0425 | 0.0540 | 0.0711 | 0.0715 | 0.0535 | 0.0792 | 0.0603 | 0.0522 | 0.0375 |
| 0.0391 | 0.0382 | 0.0318 | 0.0339 | 0.0312 | 0.0831 | 0.0403 | 0.0353 | 0.0411 | 0.0355 |
| 0.0501 | 0.0384 | 0.0371 | 0.0962 | 0.0497 | 0.0666 | 0.0398 | 0.0427 | 0.0663 | 0.0416 |
| 0.0640 | 0.0555 | 0.0796 | 0.0768 | 0.0615 | 0.0592 | 0.0946 | 0.0530 | 0.0769 | 0.0450 |
| 0.0823 | 0.0397 | 0.0567 | 0.0390 | 0.0396 | 0.0716 | 0.0423 | 0.0637 | 0.0448 | 0.3747 |
| 0.3764 | 0.4340 | 0.4833 | 0.4329 | 0.4512 | 0.4455 | 0.5192 | 0.4821 | 0.4478 | 0.4694 |
| 0.4844 | 0.5815 | 0.5309 | 0.9670 | 0.8274 | 0.7756 | 0.4701 | 0.4711 | 0.4316 | 0.4357 |
| 0.4621 | 0.4867 | 0.5287 | 0.5043 | 0.5440 | 0.5487 | 0.5110 | 0.4867 | 0.4889 | 0.5043 |
| 0.5378 | 0.5487 | 0.5400 | 1.5057 | 1.0497 | 0.9117 | 0.9334 | 0.8063 | 0.4684 | 0.4649 |
| 0.4508 | 0.3812 | 0.3495 | 0.3594 | 0.3574 | 0.3821 | 0.3640 | 0.3554 | 0.3703 | 1.0503 |
| 0.7617 | 0.5861 | 0.5539 | 0.4448 | 0.2693 | 0.2558 | 0.2740 | 0.3096 | 0.2734 | 0.2962 |

TABLE 3-continued

The training samples of DO (mg/L)

| | | | | | | | | | |
|---|---|---|---|---|---|---|---|---|---|
| 0.2997 | 0.3444 | 0.3165 | 0.2646 | 0.2404 | 0.3987 | 0.3624 | 0.3024 | 0.3268 | 0.2476 |
| 0.2465 | 0.2079 | 0.2103 | 0.2380 | 0.2519 | 0.2651 | 0.2470 | 0.2557 | 0.2890 | 0.2659 |
| 0.9111 | 0.7375 | 0.2701 | 0.2665 | 0.2489 | | | | | |

TABLE 4

The training samples of TSS (mg/L)

| | | | | | | | | | |
|---|---|---|---|---|---|---|---|---|---|
| 2.8251 | 2.7176 | 2.7700 | 2.8094 | 2.7666 | 2.7748 | 2.7823 | 2.7998 | 2.8015 | 2.7686 |
| 2.7556 | 2.7975 | 2.8011 | 2.8182 | 2.8985 | 2.8089 | 2.7813 | 2.8060 | 3.1727 | 2.9242 |
| 2.8536 | 2.8202 | 2.8179 | 2.9067 | 2.7963 | 2.8271 | 2.8168 | 2.8262 | 2.8678 | 2.8074 |
| 2.8428 | 2.8260 | 2.8615 | 2.7277 | 2.7863 | 2.8132 | 2.7385 | 2.8738 | 2.8651 | 2.9005 |
| 2.9324 | 2.8942 | 2.8223 | 2.8512 | 2.7712 | 2.6251 | 2.5540 | 2.4976 | 2.6220 | 2.6049 |
| 2.5314 | 2.5817 | 2.5765 | 2.5590 | 2.5611 | 2.5664 | 2.5177 | 2.4709 | 2.4971 | 2.4192 |
| 2.4831 | 2.5234 | 2.4654 | 2.4501 | 2.4564 | 2.4367 | 2.4777 | 2.4562 | 2.4776 | 2.4068 |
| 2.4583 | 2.4031 | 2.4443 | 2.5130 | 2.4505 | 2.4376 | 2.3933 | 2.4439 | 2.4637 | 2.4573 |
| 2.4982 | 2.5214 | 2.4515 | 2.3733 | 2.4492 | 2.4602 | 2.4725 | 2.4949 | 2.4815 | 2.5655 |
| 2.5286 | 2.4330 | 2.4429 | 2.4573 | 2.4820 | 2.6305 | 2.5025 | 2.4821 | 2.4912 | 2.4121 |
| 2.4265 | 2.4700 | 2.4481 | 2.4801 | 2.5045 | 2.4743 | 2.4331 | 2.4700 | 2.3919 | 2.4801 |
| 2.4472 | 2.4743 | 2.4740 | 2.5777 | 2.4818 | 2.5754 | 2.5450 | 2.5624 | 2.5353 | 2.4304 |
| 2.3899 | 2.3654 | 2.4347 | 2.3155 | 2.3089 | 2.2740 | 2.3947 | 2.2430 | 2.3166 | 2.2692 |
| 2.2754 | 2.3157 | 2.2768 | 2.1761 | 2.2200 | 2.1312 | 2.3333 | 2.4261 | 2.4155 | 2.3439 |
| 2.3083 | 2.3119 | 2.2717 | 2.2823 | 2.4388 | 2.4274 | 2.5251 | 2.4161 | 2.4789 | 2.3514 |
| 2.3938 | 2.2736 | 2.3829 | 2.3818 | 2.4428 | 2.4255 | 2.3938 | 2.4187 | 2.5133 | 2.4147 |
| 2.5321 | 2.4440 | 2.3300 | 2.2835 | 2.4055 | | | | | |

TABLE 5

The training samples of the effluent pH

| | | | | | | | | | |
|---|---|---|---|---|---|---|---|---|---|
| 7.9266 | 7.9298 | 7.9266 | 7.9176 | 7.8907 | 7.8718 | 7.8641 | 7.8520 | 7.8465 | 7.8448 |
| 7.8536 | 7.8579 | 7.8643 | 7.8643 | 7.8655 | 7.8645 | 7.8623 | 7.8568 | 7.8581 | 7.8595 |
| 7.8619 | 7.8632 | 7.8690 | 7.8713 | 7.8801 | 7.9154 | 7.9079 | 7.9038 | 7.9029 | 7.9466 |
| 7.9524 | 7.8931 | 7.9049 | 7.9176 | 7.9166 | 7.9110 | 7.8953 | 7.8901 | 7.8949 | 8.0150 |
| 8.0054 | 8.0039 | 7.9967 | 8.0228 | 7.9988 | 7.9917 | 7.9863 | 7.9852 | 7.9898 | 7.9908 |
| 7.9962 | 7.9949 | 7.9981 | 8.0005 | 7.9996 | 8.0042 | 8.0112 | 8.0102 | 8.0000 | 7.9967 |
| 7.9946 | 7.9947 | 7.9856 | 7.9844 | 7.9933 | 7.9970 | 7.9909 | 8.0009 | 8.0056 | 8.0036 |
| 8.0003 | 7.9993 | 8.0028 | 8.0065 | 8.0043 | 8.0035 | 8.0025 | 8.0028 | 8.0041 | 8.0044 |
| 8.0137 | 8.0184 | 8.0276 | 8.0242 | 8.0302 | 8.0337 | 8.0225 | 7.9939 | 8.0150 | 8.0210 |
| 8.0272 | 8.0274 | 8.0278 | 8.0275 | 8.0334 | 8.0398 | 8.0430 | 8.0443 | 8.0403 | 8.0348 |
| 8.0261 | 8.0217 | 8.0151 | 8.0088 | 8.0128 | 8.0119 | 7.9982 | 8.0217 | 8.0184 | 8.0088 |
| 8.0091 | 8.0119 | 8.0132 | 7.9865 | 7.9966 | 8.0214 | 8.0305 | 8.0523 | 8.0649 | 8.0616 |
| 8.0617 | 8.0597 | 8.0542 | 8.0328 | 8.0260 | 8.0137 | 8.0140 | 8.0108 | 8.0097 | 8.0142 |
| 8.0106 | 8.0296 | 8.0339 | 8.0221 | 8.0095 | 8.0303 | 8.0385 | 8.0399 | 8.0412 | 8.0335 |
| 8.0279 | 8.0111 | 7.9768 | 8.0001 | 8.0139 | 8.0204 | 8.0164 | 8.0153 | 8.0182 | 8.0221 |
| 8.0277 | 8.0347 | 8.0314 | 8.0202 | 8.0157 | 8.0092 | 8.0107 | 8.0097 | 8.0146 | 8.0159 |
| 8.0146 | 8.0166 | 8.0448 | 8.0585 | 8.0826 | | | | | |

TABLE 6

The training samples of the real effluent ammonia-nitrogen concentration (mg/L)

| | | | | | | | | | |
|---|---|---|---|---|---|---|---|---|---|
| 3.7214 | 3.6922 | 3.3211 | 3.3147 | 3.3754 | 3.4273 | 3.4585 | 3.5697 | 3.5634 | 3.6763 |
| 3.7086 | 3.6714 | 3.8618 | 3.6722 | 3.5585 | 3.6395 | 3.5802 | 3.6442 | 3.7178 | 3.8003 |
| 3.8684 | 3.9189 | 3.8830 | 3.8383 | 3.8612 | 3.6437 | 3.6019 | 3.6432 | 3.7056 | 3.6175 |
| 3.5967 | 3.5521 | 3.5992 | 3.5789 | 3.6120 | 3.5846 | 3.5920 | 3.5888 | 3.5520 | 3.7352 |
| 3.8218 | 3.9312 | 5.8870 | 5.7259 | 7.5603 | 11.9231 | 11.1773 | 12.2836 | 12.3372 | 12.3155 |
| 12.4116 | 12.5365 | 12.4893 | 12.2718 | 12.4335 | 12.3200 | 12.3238 | 12.3038 | 12.5816 | 12.4523 |
| 12.5137 | 12.7659 | 12.9055 | 12.7696 | 12.8395 | 13.1354 | 12.8835 | 12.9153 | 13.0054 | 12.9308 |
| 12.9644 | 13.0146 | 12.9466 | 13.1046 | 13.0941 | 13.0794 | 13.2232 | 13.1832 | 13.1733 | 13.2032 |
| 12.8992 | 12.7643 | 12.4099 | 12.2235 | 11.7775 | 11.5723 | 11.3341 | 11.2749 | 11.0900 | 10.9602 |
| 10.7810 | 10.7283 | 10.6037 | 9.6868 | 9.1768 | 8.9925 | 8.5913 | 8.5682 | 8.4254 | 8.3490 |
| 8.2571 | 8.2967 | 8.2521 | 8.1850 | 8.1911 | 8.1174 | 8.0427 | 8.2967 | 8.3094 | 8.1850 |
| 8.1843 | 8.1174 | 8.2504 | 7.9622 | 7.7317 | 7.4507 | 7.3742 | 6.9528 | 6.7038 | 6.3957 |
| 6.3379 | 6.3166 | 6.3299 | 6.5581 | 6.6947 | 7.0927 | 7.2973 | 7.7820 | 8.1116 | 9.0352 |
| 8.7383 | 8.7475 | 8.7663 | 8.7660 | 8.8353 | 8.8457 | 9.0967 | 9.3701 | 9.3140 | 9.0599 |
| 9.1053 | 9.2407 | 9.2865 | 9.3157 | 9.2816 | 9.3850 | 9.2125 | 8.9531 | 8.8280 | 8.5461 |
| 8.3717 | 8.1966 | 7.6552 | 9.3499 | 9.2675 | 9.2230 | 9.2480 | 9.3684 | 9.3754 | 9.2173 |
| 9.1306 | 8.8445 | 7.5305 | 7.1104 | 6.5671 | | | | | |

TABLE 7

The outputs of the recurrent self-organizing neural network in the training process (mg/L)

| | | | | | | | | | |
|---|---|---|---|---|---|---|---|---|---|
| 3.7842 | 3.6955 | 3.4035 | 3.1000 | 3.4514 | 3.5299 | 3.4003 | 3.3512 | 3.6258 | 3.7517 |
| 3.6886 | 3.5692 | 4.0296 | 3.7519 | 3.7126 | 3.8381 | 3.8528 | 3.2400 | 3.6796 | 3.8111 |
| 3.8598 | 3.7948 | 3.7933 | 3.8403 | 3.8687 | 3.8490 | 3.4309 | 3.5505 | 3.5864 | 3.6058 |
| 3.6033 | 3.5463 | 3.4731 | 3.4313 | 3.5456 | 4.0032 | 3.7263 | 3.6194 | 3.5477 | 3.7518 |
| 3.8272 | 3.9173 | 5.8444 | 5.7479 | 7.5665 | 11.8148 | 12.1198 | 12.3419 | 12.3674 | 12.2235 |
| 12.4819 | 12.5644 | 12.5330 | 12.3365 | 12.4200 | 12.3603 | 12.4098 | 12.2661 | 12.5402 | 12.4473 |
| 12.5159 | 12.8958 | 12.7052 | 12.9661 | 13.0068 | 13.1035 | 12.6238 | 13.1129 | 12.6902 | 12.9062 |
| 12.7613 | 13.1369 | 13.0705 | 13.0488 | 13.2949 | 12.9133 | 12.9525 | 13.0572 | 13.3742 | 13.3882 |
| 12.7594 | 12.8822 | 12.4131 | 12.0293 | 10.3936 | 11.5563 | 10.6390 | 11.0043 | 11.1370 | 11.1234 |
| 10.2559 | 11.0945 | 10.4768 | 9.7053 | 9.1992 | 9.0008 | 8.7348 | 8.8083 | 8.5365 | 8.6181 |
| 8.7525 | 8.7364 | 8.0552 | 8.3347 | 8.3500 | 8.1183 | 8.1562 | 8.7374 | 8.2457 | 8.3358 |
| 7.8597 | 8.1193 | 8.3285 | 7.9669 | 7.7341 | 7.4802 | 7.3175 | 6.9490 | 6.6141 | 6.4781 |
| 6.4584 | 6.8932 | 6.6881 | 6.6964 | 6.8403 | 6.9678 | 7.4339 | 7.9103 | 7.9315 | 9.0342 |
| 8.7332 | 8.6464 | 8.8931 | 8.7614 | 8.8156 | 8.7724 | 8.7067 | 9.3423 | 8.3514 | 8.7110 |
| 9.2627 | 9.1725 | 9.3982 | 9.2134 | 8.9834 | 9.4617 | 9.1733 | 8.8833 | 9.0942 | 8.7205 |
| 8.0875 | 8.3975 | 8.1150 | 9.2811 | 9.7516 | 9.6039 | 9.3939 | 9.1582 | 9.3664 | 9.3410 |
| 9.1240 | 8.9294 | 7.7141 | 7.1464 | 6.5466 | | | | | |

TABLE 8

The testing samples of TP (mg/L)

| | | | | | | | | | |
|---|---|---|---|---|---|---|---|---|---|
| 3.9522 | 4.1867 | 4.5942 | 4.5057 | 4.5057 | 4.0066 | 3.7529 | 4.1116 | 4.1465 | 4.1465 |
| 4.1465 | 4.0993 | 4.2017 | 4.5199 | 4.1266 | 4.2198 | 3.4877 | 4.7860 | 3.9951 | 4.3522 |
| 4.4541 | 4.1859 | 4.2168 | 3.9868 | 3.9029 | 4.0702 | 4.1378 | 4.3289 | 4.3061 | 4.0605 |
| 4.1268 | 3.9708 | 3.9485 | 4.0112 | 4.1164 | 4.3104 | 4.0388 | 3.8027 | 3.7678 | 4.0382 |
| 4.2339 | 4.2524 | 4.1057 | 3.9310 | 3.9415 | 3.8455 | 4.3598 | 4.2394 | 4.2394 | 4.2394 |
| 4.2394 | 4.2392 | 4.2392 | 4.2392 | 4.2889 | 3.9926 | 4.1127 | 4.0208 | 4.1534 | 4.2663 |
| 4.2058 | 4.0359 | 3.8457 | 3.7628 | 3.9413 | 4.0122 | 3.9671 | 3.9380 | 3.9573 | 3.7158 |
| 3.6388 | 3.6132 | 3.8164 | 3.9993 | 3.9670 | 4.0034 | 4.1387 | 4.1678 | 3.9797 | 4.2248 |

TABLE 9

The testing samples of ORP

| | | | | | | | | | |
|---|---|---|---|---|---|---|---|---|---|
| 552.1540 | 556.8970 | 551.9620 | 552.6030 | 558.6280 | 561.4480 | 543.7580 | 565.7420 | 565.0370 | 564.2680 |
| 565.2930 | 564.3960 | 565.9980 | 489.0880 | 558.1790 | 558.8200 | 487.6130 | 568.9460 | 565.5500 | 580.4190 |
| 581.5730 | 581.7010 | 582.0850 | 581.1880 | 580.0980 | 579.7780 | 580.6110 | 580.7390 | 580.1630 | 579.8420 |
| 578.1120 | 579.3930 | 578.2400 | 578.1760 | 577.5990 | 577.0860 | 576.7020 | 573.6890 | 574.7150 | 574.7790 |
| 575.0350 | 572.1510 | 572.8560 | 571.6380 | 573.7530 | 574.0100 | 575.3560 | 575.2920 | 574.8430 | 574.0100 |
| 573.7530 | 574.5860 | 573.9460 | 573.3050 | 570.4210 | 570.0360 | 572.0230 | 572.2150 | 573.4970 | 572.9840 |
| 572.9840 | 573.3050 | 577.3420 | 578.5600 | 570.6130 | 571.5740 | 570.9970 | 569.9080 | 567.6650 | 569.0100 |
| 569.3310 | 569.4590 | 570.6130 | 572.8560 | 571.4460 | 570.6130 | 569.8440 | 569.3950 | 570.2920 | 571.1900 |

TABLE 10

The testing samples of DO (mg/L)

| | | | | | | | | | |
|---|---|---|---|---|---|---|---|---|---|
| 0.0383 | 0.0428 | 0.0361 | 0.0378 | 0.0395 | 0.0602 | 0.0706 | 0.0453 | 0.0743 | 0.0735 |
| 0.0567 | 0.1172 | 0.0582 | 0.0398 | 0.0609 | 0.0811 | 0.0686 | 0.0398 | 0.0474 | 0.0317 |
| 0.0298 | 0.1265 | 0.0659 | 0.0971 | 0.0345 | 0.0355 | 0.0457 | 0.0488 | 0.0412 | 0.0545 |
| 0.0765 | 0.0364 | 0.0406 | 0.0843 | 0.0464 | 0.0346 | 0.1481 | 0.4026 | 0.3942 | 0.4193 |
| 0.4073 | 0.4379 | 0.5426 | 0.5498 | 0.8550 | 0.4882 | 0.4207 | 0.4564 | 0.4889 | 0.5378 |
| 0.5400 | 0.5287 | 0.5440 | 0.5110 | 0.8817 | 0.8742 | 0.4291 | 0.4537 | 0.3765 | 0.3696 |
| 0.3782 | 0.3274 | 0.7197 | 0.5351 | 0.2611 | 0.3343 | 0.3412 | 0.3301 | 0.2746 | 0.2365 |
| 0.3272 | 0.2974 | 0.2066 | 0.1995 | 0.2546 | 0.2459 | 0.2654 | 0.2566 | 0.2232 | 0.2282 |

TABLE 11

The testing samples of TSS (mg/L)

| | | | | | | | | | |
|---|---|---|---|---|---|---|---|---|---|
| 2.8343 | 2.8151 | 2.7787 | 2.7807 | 2.7539 | 2.7827 | 2.8063 | 2.8055 | 2.9044 | 2.8029 |
| 2.7963 | 2.8936 | 2.8786 | 2.8337 | 2.7973 | 2.7974 | 2.8266 | 2.8632 | 2.9151 | 2.7774 |
| 2.8432 | 2.7067 | 2.6005 | 2.6635 | 2.5869 | 2.5829 | 2.5363 | 2.5279 | 2.4897 | 2.4674 |
| 2.4916 | 2.5265 | 2.5397 | 2.4082 | 2.4903 | 2.3932 | 2.4240 | 2.4906 | 2.5340 | 2.3839 |
| 2.4320 | 2.3993 | 2.5394 | 2.5140 | 2.4693 | 2.4245 | 2.4605 | 2.4649 | 2.3919 | 2.4472 |
| 2.4740 | 2.4481 | 2.5045 | 2.4331 | 2.4866 | 2.5113 | 2.4309 | 2.3655 | 2.3883 | 2.2805 |

TABLE 11-continued

The testing samples of TSS (mg/L)

| | | | | | | | | | |
|---|---|---|---|---|---|---|---|---|---|
| 2.3078 | 2.2824 | 2.2668 | 2.2297 | 2.2105 | 2.4196 | 2.2935 | 2.3671 | 2.3100 | 2.3821 |
| 2.4491 | 2.5777 | 2.4440 | 2.4318 | 2.4089 | 2.4784 | 2.4254 | 2.4256 | 2.3243 | 2.3120 |

TABLE 12

The testing samples of the effluent pH

| | | | | | | | | | |
|---|---|---|---|---|---|---|---|---|---|
| 7.9298 | 7.9087 | 7.8818 | 7.8586 | 7.8445 | 7.8517 | 7.8622 | 7.8667 | 7.8590 | 7.8593 |
| 7.8643 | 7.8702 | 7.9216 | 7.9536 | 7.9188 | 7.9032 | 7.8936 | 8.0238 | 8.0090 | 7.9940 |
| 8.0011 | 8.0101 | 7.9908 | 7.9930 | 7.9959 | 7.9983 | 8.0112 | 8.0045 | 7.9968 | 7.9936 |
| 7.9866 | 8.0030 | 8.0069 | 7.9992 | 8.0040 | 8.0033 | 8.0015 | 8.0090 | 8.0264 | 8.0254 |
| 8.0373 | 8.0021 | 8.0281 | 8.0288 | 8.0305 | 8.0431 | 8.0480 | 8.0316 | 8.0184 | 8.0091 |
| 8.0132 | 8.0151 | 8.0128 | 7.9982 | 8.0055 | 8.0419 | 8.0627 | 8.0595 | 8.0498 | 8.0158 |
| 8.0107 | 8.0120 | 8.0195 | 8.0314 | 8.0187 | 8.0398 | 8.0368 | 8.0281 | 7.9850 | 8.0196 |
| 8.0101 | 8.0212 | 8.0334 | 8.0235 | 8.0123 | 8.0105 | 8.0145 | 8.0124 | 8.0209 | 8.0745 |

TABLE 13

The testing samples of the real effluent ammonia-nitrogen concentration (mg/L)

| | | | | | | | | | |
|---|---|---|---|---|---|---|---|---|---|
| 3.5761 | 3.3048 | 3.4170 | 3.5679 | 3.5392 | 3.9342 | 3.5926 | 3.5754 | 3.5805 | 3.7210 |
| 3.9394 | 3.9206 | 3.7720 | 3.5899 | 3.5946 | 3.5928 | 3.5704 | 3.6951 | 3.7283 | 6.8643 |
| 7.6531 | 9.9438 | 12.0870 | 12.4108 | 12.2645 | 12.2824 | 12.3406 | 12.3668 | 12.5197 | 12.6702 |
| 12.7935 | 13.0679 | 12.9323 | 12.9189 | 13.1193 | 13.2119 | 13.1942 | 13.0278 | 12.5932 | 12.0214 |
| 11.5033 | 11.1842 | 10.8915 | 10.6223 | 9.3917 | 8.7883 | 8.5280 | 8.2748 | 8.3094 | 8.1843 |
| 8.2504 | 8.2521 | 8.1911 | 8.0427 | 7.6784 | 7.1995 | 6.5172 | 6.3016 | 6.3704 | 6.7937 |
| 7.6118 | 8.3032 | 8.7825 | 8.7420 | 8.7893 | 9.5518 | 9.2179 | 9.1266 | 9.2621 | 9.2021 |
| 9.0655 | 8.6186 | 8.2710 | 7.5227 | 9.3176 | 9.1937 | 9.2926 | 9.0822 | 8.6282 | 6.8153 |

TABLE 14

The outputs of the recurrent self-organizing neural network in the testing process (mg/L)

| | | | | | | | | | |
|---|---|---|---|---|---|---|---|---|---|
| 3.0054 | 2.9792 | 4.1867 | 4.9286 | 4.2662 | 5.2209 | 4.8830 | 5.9236 | 4.0377 | 5.6451 |
| 6.2735 | 6.2896 | 4.7227 | 2.5800 | 2.4380 | 4.1350 | 2.3930 | 11.5193 | 5.2214 | 6.0038 |
| 5.9712 | 13.0544 | 10.9030 | 19.2732 | 12.8016 | 12.1521 | 12.1938 | 11.9632 | 12.8526 | 13.2788 |
| 12.6482 | 13.3323 | 12.9681 | 12.9030 | 13.3655 | 16.1601 | 11.5984 | 13.6644 | 13.0311 | 12.4301 |
| 9.8375 | 9.5739 | 10.0693 | 7.9654 | 10.2654 | 12.5032 | 10.2643 | 9.0101 | 7.8697 | 6.7043 |
| 7.0017 | 6.9231 | 6.9281 | 7.3861 | 5.1751 | 5.5377 | 7.3165 | 8.5132 | 7.9163 | 6.5856 |
| 6.6081 | 7.9339 | 8.8676 | 6.0381 | 9.3639 | 9.1078 | 9.9013 | 9.6566 | 9.9644 | 8.8577 |
| 7.8352 | 6.3314 | 7.5965 | 9.2300 | 9.5224 | 10.2648 | 9.0901 | 9.1036 | 9.1942 | 4.3949 |

The present invention has been described using exemplary embodiments. However, it is to be understood that the scope of the present invention is not limited to the disclosed embodiments. On the contrary, it is intended to cover various modifications and similar arrangement or equivalents which can be obtained by a person skilled in the art without creative work or undue experimentation. The scope of the claims, therefore, should be accorded the broadest interpretation so as to encompass all such modifications and similar arrangements and equivalents.

We claim:

1. A method for predicting effluent ammonia-nitrogen concentration in wastewater based on a recurrent self-organizing neural network, comprising:

(1) providing training samples, each training sample including input variables as measured parameters of a wastewater and a measured effluent ammonia-nitrogen concentration of the wastewater;

(2) designing a topological structure of a recurrent self-organizing neural network having an input layer, a hidden layer and an output layer, wherein an initial structure of the recurrent self-organizing neural network is M-K-1, having M nodes in the input layer, K nodes in the hidden layer and 1 node in the output layer, where M>3 is a positive integer and represents the number of the input variables, K>2 is a positive integer;

wherein an input vector of the recurrent self-organizing neural network is $u(t)=[u_1(t), u_2(t), \ldots, u_M(t)]$ at time t, where $u_1(t)$ is the value of input variable 1, $u_2(t)$ is the value of input variable 2, and $u_M(t)$ is the value of input variable M, respectively, at time t;

the output, y(t), of the recurrent self-organizing neural network, which is the calculated value of the effluent ammonia-nitrogen concentration at time t, is expressed as:

$$y(t) = \sum_{k=1}^{K} w_k^3(t) v_k(t), \qquad (1)$$

where $w_k^3(t)$ is connecting weight between kth node in the hidden layer and the node in the output layer at time t, where k=1, 2, ..., K; and $v_k(t)$ is the output of kth node in the hidden layer at time t:

$$v_k(t) = f\left(\sum_{m=1}^{M} w_{mk}^1(t)u_m(t) + v_k^1(t)\right), \quad (2)$$

where $w_{mk}^1(t)$ is connecting weight between mth node in the input layer and kth node in the hidden layer at time t, m=1, 2, ..., M; $v_k^1(t)$ is feedback value of kth node in the hidden layer at time t which can be expressed as:

$$v_k^1(t) = w_k^2(t)v_k(t-1), \quad (3)$$

where $w_k^2(t)$ is self-feedback weight of kth node in the hidden layer at time t, $v_k(t-1)$ is the output of kth node in the hidden layer at time t−1;

wherein a root-mean-squared error is defined as:

$$E(t) = \frac{1}{2T}\sum_{t=1}^{T}(y_d(t) - y(t))^2, \quad (4)$$

where $y_d(t)$ is the real value of the effluent ammonia-nitrogen concentration at time t and T is the number of training samples;

(3) training the recurrent self-organizing neural network,

① initializing the connecting weight between the nodes in the hidden layer and the node in the output layer, the self-feedback weight of the nodes in the hidden layer, and the connecting weight between the nodes in the input layer and the nodes in the hidden layer, $w_k^3(t)\in(0, 1)$, $w_k^2(t)\in(0, 1)$, and $w_{mk}^1(t)\in(0, 1)$, m=1, 2, ..., M, k=1, 2, ..., K, and pre-setting an expected error value $E_d$, $E_d\in(0, 0.01]$;

② calculating the total sensitivity of the nodes in the hidden layer, respectively, as follows:

$$ST_k(t) = \frac{\text{Var}_k[E(y(t)|v_k(t))]}{\text{Var}[y(t)]}, \quad (5)$$

where $$\text{Var}_k[E(y(t)|v_k(t))] = 2(A_k)^2 + (B_k)^2, \quad (6)$$

$$\text{Var}(y(t)) = 2\sum_{k=1}^{K}((A_k)^2 + (B_k)^2),$$

k=1, 2, ..., K; $A_k$ and $B_k$ are Fourier coefficients which are given by:

$$A_k = \frac{1}{2\pi}\int_{-\pi}^{\pi}\cos(\omega_k(t)s)ds, \quad (7)$$

$$B_k = \frac{1}{2\pi}\int_{-\pi}^{\pi}\sin(\omega_k(t)s)ds,$$

where the range of s is $[-\pi, \pi]$; $\omega_k(t)$ is the frequency of kth node in the hidden layer, $\omega_k(t)$ is determined by the output of kth node in the hidden layer as follows:

$$\omega_k(t) = \arcsin\frac{\pi}{b_k(t) - a_k(t)}\left(v_k(t) - \frac{b_k(t) + a_k(t)}{2}\right), \quad (8)$$

where $b_k(t)$ is the maximum output of the kth node in the hidden layer during the training process, $a_k(t)$ is the minimum output of the kth node in the hidden layer during the training process;

③ tuning the structure of the recurrent self-organizing neural network pruning step: if the total sensitivity $ST_k(t)<\alpha_1$, $\alpha_1\in(0, 0.01]$, the kth node in the hidden layer will be pruned, the number of nodes in the hidden layer is updated, and $K_1=K-1$; otherwise, the kth node in the hidden layer will not be pruned, and $K_1=K$;

growing step: if the root-mean-squared error $E(t)>E_d$, a new node will be added to the hidden layer, and an initial weight of the new node added to the hidden layer is given by:

$$w_{new}^1(t) = w_h^1(t) = [w_{1h}^1(t), w_{2h}^1(t), \ldots, w_{5h}^1(t)], \quad (9)$$

$$w_{new}^2(t) = w_h^2(t),$$

$$w_{new}^3(t) = \frac{y_d(t) - y(t)}{v_{new}(t)},$$

where $w_{new}^1(t)$ is connecting weight vector between the new node added to the hidden layer and the input layer, $w_{new}^2(t)$ is self-feedback weight of the new node added to the hidden layer, $w_{new}^3(t)$ is connecting weight between the new node added to the hidden layer and the output layer, h node is the node in the hidden layer which has the largest total sensitivity, $w_h^1(t)$ is connecting weight vector between the hth node in the hidden layer and the input layer before adding the new node to the hidden layer, $w_h^2(t)$ is self-feedback weight of the hth node in the hidden layer before adding the new node to the hidden layer, and the output of the new node added to the hidden layer is defined as:

$$v_{new}(t) = f\left(\sum_{m=1}^{M} w_{mh}^1(t)u_m(t) + v_{new}^1(t)\right), \quad (10)$$

$$v_{new}^1(t) = w_h^2(t)v_h(t-1),$$

and the number of nodes in the hidden layer is updated, $K_2=K_1+1$;

otherwise, the structure of the recurrent self-organizing neural network will not be adjusted, and $K_2=K_1$;

④ updating the weights $w_k^1(t)$, $w_k^2(t)$ and $w_k^3(t)$ the adaptation strategies of weights is defined as:

$$w_k^1(t+1) = w_k^1(t) + \eta_1\frac{\partial E(t)}{\partial w_k^1(t)}, \quad (11)$$

$$w_k^2(t+1) = w_k^2(t) + \eta_2\frac{\partial E(t)}{\partial w_k^2(t)},$$

$$w_k^3(t+1) = w_k^3(t) + \eta_3\frac{\partial E(t)}{\partial w_k^3(t)},$$

where k=1, 2, ..., $K_2$; $w_k^1(t)=[w_{1k}^1(t), w_{2k}^1(t), \ldots, w_{Mk}^1(t)]$, $\eta_1\in(0, 0.1]$, $\eta_2\in(0, 0.1]$ and $\eta_3\in(0, 0.01]$ are respectively the learning rate of the connection weights between the input layer and the hidden layer, the learning rate of the self-feedback weight in the hidden layer, and the learning rate of the connection weights between the hidden layer and the output layer;

(5) importing training sample x(t+1), and repeating steps (2)-(4), then, stopping the training process after all of the training samples are imported to the recurrent self-organizing neural network so as to obtain a trained recurrent self-organizing neural network;

(4) providing the same input variables of a wastewater to be monitored as that of the training samples, and inputting the input variables of the wastewater to be monitored to the trained recurrent self-organizing neural network to carry out calculation, wherein the output of the trained recurrent self-organizing neural network is the predicted value of the effluent ammonia-nitrogen concentration of the wastewater to be monitored.

2. The method for predicting effluent ammonia-nitrogen concentration in wastewater based on a recurrent self-organizing neural network according to claim 1, wherein the number of the input variables, M, is in the range of 4-8, and the input variables include total phosphorus (TP), oxidation reduction potential (ORP), dissolved oxygen (DO), total suspended solids (TSS), effluent pH, temperature, influent rate, and sludge volume index (SVI) of the wastewater.

3. The method for predicting effluent ammonia-nitrogen concentration in wastewater based on a recurrent self-organizing neural network according to claim 2, wherein the number of the input variables, M, is 5, and the input variables are the total phosphorus (TP), the oxidation reduction potential (ORP), the dissolved oxygen (DO), the total suspended solids (TSS), and the effluent pH of the wastewater.

4. The method for predicting effluent ammonia-nitrogen concentration in wastewater based on a recurrent self-organizing neural network according to claim 1, wherein step (4) is repeated in a predetermined interval by providing real-time measured input variables of the wastewater to be monitored, and inputting the input variables to the trained recurrent self-organizing neural network to carry out calculation, so that predicted values of the effluent ammonia-nitrogen concentration of the wastewater to be monitored are obtained continuously with time.

5. The method for predicting effluent ammonia-nitrogen concentration in wastewater based on a recurrent self-organizing neural network according to claim 1, wherein the number of the training samples used for training the recurrent self-organizing neural network is in the range of 100-300.

6. The method for predicting effluent ammonia-nitrogen concentration in wastewater based on a recurrent self-organizing neural network according to claim 1, wherein the training samples comprise training samples taken from the wastewater to be monitored.

7. The method for predicting effluent ammonia-nitrogen concentration in wastewater based on a recurrent self-organizing neural network according to claim 1, further comprising on-line training the recurrent self-organizing neural network using training samples taken from the wastewater to be monitored in the process of predicting the effluent ammonia-nitrogen concentration in the wastewater to be monitored.

8. A method for on-line real-time monitoring effluent ammonia-nitrogen concentration in wastewater comprising:
    providing a trained recurrent self-organizing neural network;

real-time measuring parameters of the wastewater to be monitored, which are used as input variables of the trained recurrent self-organizing neural network;

inputting the input variables to the trained recurrent self-organizing neural network to carry out calculation, wherein the output of the trained recurrent self-organizing neural network is the predicted value of the effluent ammonia-nitrogen concentration of the wastewater to be monitored;

repeating the real-time measuring parameters step and the inputting the input variables step by real-time measuring the parameters of the wastewater to be monitored, and inputting the input variables to the trained recurrent self-organizing neural network to carry out calculation in a predetermined interval, so that predicted values of the effluent ammonia-nitrogen concentration of the wastewater to be monitored are obtained continuously with time;

wherein the trained recurrent self-organizing neural network is obtained by:

(1) providing training samples, each training sample including input variables as measured parameters of a wastewater and a measured effluent ammonia-nitrogen concentration of the wastewater;

(2) designing a topological structure of a recurrent self-organizing neural network having an input layer, a hidden layer and an output layer, wherein an initial structure of the recurrent self-organizing neural network is M-K-1, having M nodes in the input layer, K nodes in the hidden layer and 1 node in the output layer, where M>3 is a positive integer and represents the number of the input variables, K>2 is a positive integer;

wherein an input vector of the recurrent self-organizing neural network is u(t)=[$u_1(t)$, $u_2(t)$, . . . , $u_M(t)$] at time t, where $u_1(t)$ is the value of input variable 1, $u_2(t)$ is the value of input variable 2, and $u_M(t)$ is the value of input variable M, respectively, at time t;

the output, y(t), of the recurrent self-organizing neural network, which is the calculated value of the effluent ammonia-nitrogen concentration at time t, is expressed as:

$$y(t) = \sum_{k=1}^{K} w_k^3(t) v_k(t), \qquad (1)$$

where $w_k^3(t)$ is connecting weight between kth node in the hidden layer and the node in the output layer at time t, where k=1, 2, . . . , K; and $v_k(t)$ is the output of kth node in the hidden layer at time t:

$$v_k(t) = f\left(\sum_{m=1}^{M} w_{mk}^1(t) u_m(t) + v_k^1(t)\right), \qquad (2)$$

where $w_{mk}^1(t)$ is connecting weight between mth node in the input layer and kth node in the hidden layer at time t, m=1, 2, . . . , M; $v_k^1(t)$ is feedback value of kth node in the hidden layer at time t which can be expressed as:

$$v_k^1(t) = w_k^2(t) v_k(t-1), \qquad (3)$$

where $w_k^2(t)$ is self-feedback weight of kth node in the hidden layer at time t, $v_k(t-1)$ is the output of kth node in the hidden layer at time t−1;

wherein a root-mean-squared error is defined as:

$$E(t) = \frac{1}{2T}\sum_{t=1}^{T}(y_d(t) - y(t))^2, \quad (4)$$

where $y_d(t)$ is the real value of the effluent ammonia-nitrogen concentration at time t and T is the number of training samples;

(3) training the recurrent self-organizing neural network,

① initializing the connecting weight between the nodes in the hidden layer and the node in the output layer, the self-feedback weight of the nodes in the hidden layer, and the connecting weight between the nodes in the input layer and the nodes in the hidden layer, $w_k^3(t)\in(0, 1)$, $w_k^2(t)\in(0, 1)$, and $w_{mk}^1(t)\in(0, 1)$, m=1, 2, ..., M, k=1, 2, ..., K, and pre-setting an expected error value $E_d$, $E_d\in(0, 0.01]$;

② calculating the total sensitivity of the nodes in the hidden layer, respectively, as follows:

$$ST_k(t) = \frac{\mathrm{Var}_k[E(y(t)\mid v_k(t))]}{\mathrm{Var}[y(t)]}, \quad (5)$$

where $$\mathrm{Var}_k[E(y(t)\mid v_k(t))] = 2(A_k)^2 + (B_k)^2, \quad (6)$$

$$\mathrm{Var}(y(t)) = 2\sum_{k=1}^{K}((A_k)^2 + (B_k)^2),$$

k=1, 2, ..., K; $A_k$ and $B_k$ are Fourier coefficients which are given by:

$$A_k = \frac{1}{2\pi}\int_{-\pi}^{\pi}\cos(\omega_k(t)s)\,ds, \quad (7)$$

$$B_k = \frac{1}{2\pi}\int_{-\pi}^{\pi}\sin(\omega_k(t)s)\,ds,$$

where the range of s is $[-\pi, \pi]$; $\omega_k(t)$ is the frequency of kth node in the hidden layer, $\omega_k(t)$ is determined by the output of kth node in the hidden layer as follows:

$$\omega_k(t) = \arcsin\frac{\pi}{b_k(t) - a_k(t)}\left(v_k(t) - \frac{b_k(t) + a_k(t)}{2}\right), \quad (8)$$

where $b_k(t)$ is the maximum output of the kth node in the hidden layer during the training process, $a_k(t)$ is the minimum output of the kth node in the hidden layer during the training process;

③ tuning the structure of the recurrent self-organizing neural network pruning step: if the total sensitivity $ST_k(t)<\alpha_1$, $\alpha_1\in(0, 0.01]$, the kth node in the hidden layer will be pruned, the number of nodes in the hidden layer is updated, and $K_1=K-1$; otherwise, the kth node in the hidden layer will not be pruned, and $K_1=K$;

growing step: if the root-mean-squared error $E(t)>E_d$, a new node will be added to the hidden layer, and an initial weight of the new node added to the hidden layer is given by:

$$w_{new}^1(t) = w_h^1(t) = [w_{1h}^1(t), w_{2h}^1(t), \ldots, w_{5h}^1(t)], \quad (9)$$

$$w_{new}^2(t) = w_h^2(t),$$

$$w_{new}^3(t) = \frac{y_d(t) - y(t)}{v_{new}(t)},$$

where $w_{new}^1(t)$ is connecting weight vector between the new node added to the hidden layer and the input layer, $w_{new}^2(t)$ is self-feedback weight of the new node added to the hidden layer, $w_{new}^3(t)$ is connecting weight between the new node added to the hidden layer and the output layer, h node is the node in the hidden layer which has the largest total sensitivity, $w_h^1(t)$ is connecting weight vector between the hth node in the hidden layer and the input layer before adding the new node to the hidden layer, $w_h^2(t)$ is self-feedback weight of the hth node in the hidden layer before adding the new node to the hidden layer, and the output of the new node added to the hidden layer is defined as:

$$v_{new}(t) = f\left(\sum_{m=1}^{M}w_{mh}^1(t)u_m(t) + v_{new}^1(t)\right), \quad (10)$$

$$v_{new}^1(t) = w_h^2(t)v_h(t-1),$$

and the number of nodes in the hidden layer is updated, $K_2=K_1+1$;

otherwise, the structure of the recurrent self-organizing neural network will not be adjusted, and $K_2=K_1$;

④ updating the weights $w_k^1(t)$, $w_k^2(t)$ and $w_k^3(t)$ the adaptation strategies of weights is defined as:

$$w_k^1(t+1) = w_k^1(t) + \eta_1\frac{\partial E(t)}{\partial w_k^1(t)}, \quad (11)$$

$$w_k^2(t+1) = w_k^2(t) + \eta_2\frac{\partial E(t)}{\partial w_k^2(t)},$$

$$w_k^3(t+1) = w_k^3(t) + \eta_3\frac{\partial E(t)}{\partial w_k^3(t)},$$

where k=1, 2, ..., $K_2$; $w_k^1(t)=[w_{1k}^1(t), w_{2k}^1(t), \ldots, w_{Mk}^1(t)]$, $\eta_1\in(0, 0.1]$, $\eta_2\in(0, 0.1]$ and $\eta_3\in(0, 0.01]$ are respectively the learning rate of the connection weights between the input layer and the hidden layer, the learning rate of the self-feedback weight in the hidden layer, and the learning rate of the connection weights between the hidden layer and the output layer;

⑤ importing training sample x(t+1), and repeating steps ②-④, then, stopping the training process after all of the training samples are imported to the recurrent self-organizing neural network so as to obtain the trained recurrent self-organizing neural network.

9. The method for predicting effluent ammonia-nitrogen concentration in wastewater based on a recurrent self-organizing neural network according to claim 8, wherein the number of the input variables, M, is in the range of 4-8, and the input variables include total phosphorus (TP), oxidation reduction potential (ORP), dissolved oxygen (DO), total suspended solids (TSS), effluent pH, temperature, influent rate, and sludge volume index (SVI) of the wastewater.

10. The method for predicting effluent ammonia-nitrogen concentration in wastewater based on a recurrent self-organizing neural network according to claim 9, wherein the number of the input variables, M, is 5, and the input variables are the total phosphorus (TP), the oxidation reduction potential (ORP), the dissolved oxygen (DO), the total suspended solids (TSS), and the effluent pH of the wastewater.

11. The method for predicting effluent ammonia-nitrogen concentration in wastewater based on a recurrent self-organizing neural network according to claim 8, wherein the inputting the input variables step is repeated every 0.5-5 min by using corresponding real-time measured parameters of the wastewater as the input variables.

12. The method for predicting effluent ammonia-nitrogen concentration in wastewater based on a recurrent self-organizing neural network according to claim 8, further comprising on-line retraining the trained recurrent self-organizing neural network by using training samples taken from the wastewater to be monitored in the process of on-line predicting the effluent ammonia-nitrogen concentration in the wastewater to be monitored.

* * * * *